United States Patent
Gupta et al.

(10) Patent No.: US 11,583,517 B2
(45) Date of Patent: Feb. 21, 2023

(54) DUAL ANTAGONIST OF PGD$_2$/DPR2 AND THROMBOXANE A$_2$/TPR RECEPTORS AND USE FOR TREATMENT OF MALADAPTIVE IMMUNE RESPONSE OR THROMBOTIC DIATHESIS

(71) Applicant: APPLIED MEDICAL TECHNOLOGIES LLC, Las Vegas, NV (US)

(72) Inventors: Ajay Gupta, Orange, CA (US); Kate Chander Chiang, Rossmoor, CA (US)

(73) Assignee: APPLIED MEDICAL TECHNOLOGIES LLC, Las Vegas, NV (US)

( * ) Notice: Subject to any disclaimer, the term of this patent is extended or adjusted under 35 U.S.C. 154(b) by 0 days.

(21) Appl. No.: 17/566,089

(22) Filed: Dec. 30, 2021

(65) Prior Publication Data

US 2022/0184031 A1 Jun. 16, 2022

Related U.S. Application Data

(63) Continuation of application No. PCT/IB2021/052693, filed on Mar. 31, 2021.

(60) Provisional application No. 63/092,921, filed on Oct. 16, 2020, provisional application No. 63/027,751, filed on May 20, 2020, provisional application No. 63/005,205, filed on Apr. 3, 2020, provisional application No. 63/003,286, filed on Mar. 31, 2020.

(51) Int. Cl.
*A61K 31/40* (2006.01)
*A61K 31/403* (2006.01)
*A61P 11/00* (2006.01)
*A61K 31/573* (2006.01)
*A61K 45/06* (2006.01)

(52) U.S. Cl.
CPC .......... *A61K 31/403* (2013.01); *A61K 31/573* (2013.01); *A61K 45/06* (2013.01); *A61P 11/00* (2018.01)

(58) Field of Classification Search
CPC ..................................................... A61K 31/40
USPC .......................................................... 514/411
See application file for complete search history.

(56) References Cited

FOREIGN PATENT DOCUMENTS

WO 2016/102352 6/2016
WO 2019/108736 6/2019

OTHER PUBLICATIONS

ISR for International Application PCT/IB2021/052693 dated Sep. 14, 2021.
Written Opinion for International Application PCT/IB2021/052693 dated Sep. 14, 2021.
Ajay Gupta, et al.: Ramatroban as a Novel Immunotherapy for COVID-19: J Mol Genet Med. 2020: 14(3): pp. 1-9: doi:10.37421/jmgm.2020.14.457.
Moon TC et al., "Expression of DP2 (CRTh2), a prostaglandin D$_2$ receptor, in human mast cells," PLoS One. Sep. 30, 2014;9(9):e108595. doi: 10.1371/journal.pone.0108595. eCollection 2014. PMID: 25268140.
Liu H et al., "Molecular basis for lipid recognition by the prostaglandin D2 receptor CRTH2," Proc Natl Acad Sci U S A. Aug. 10, 2021;118(32):e2102813118. doi: 10.1073/pnas.2102813118. PMID: 34341104.
Ishizuka T et al. (BAY u 3405): a novel dual antagonist of TXA2 receptor and CRTh2, a newly identified prostaglandin D2 receptor. Cardiovascular drug reviews. Jun. 2004;22(2):71-90.
Krishna Deepak RN et al. Recent Advances in Structure, Function, and Pharmacology of Class A Lipid GPCRs: Opportunities and Challenges for Drug Discovery. Pharmaceuticals Dec. 22, 2021;15(1):12.
Mesquita-Santos FP et al. Co-operative signalling through DP1 and DP2 prostanoid receptors is required to enhance leukotriene C4 synthesis induced by prostaglandin D2 in eosinophils. British journal of pharmacology. Apr. 2011;162(8):1674-85.

*Primary Examiner* — Raymond J Henley, III
(74) *Attorney, Agent, or Firm* — Ladas & Parry LLP

(57) ABSTRACT

The present invention relates to a pharmaceutical composition for treatment of a disease or condition characterized by or associated with stimulation of both DPr2 and TPr signaling, said composition comprising an effective amount of a dual receptor antagonist of DPr$_2$ for prostaglandin D$_2$ and TPr for thromboxane A$_2$ and a pharmaceutically acceptable carrier.

26 Claims, 3 Drawing Sheets

Figure 1:
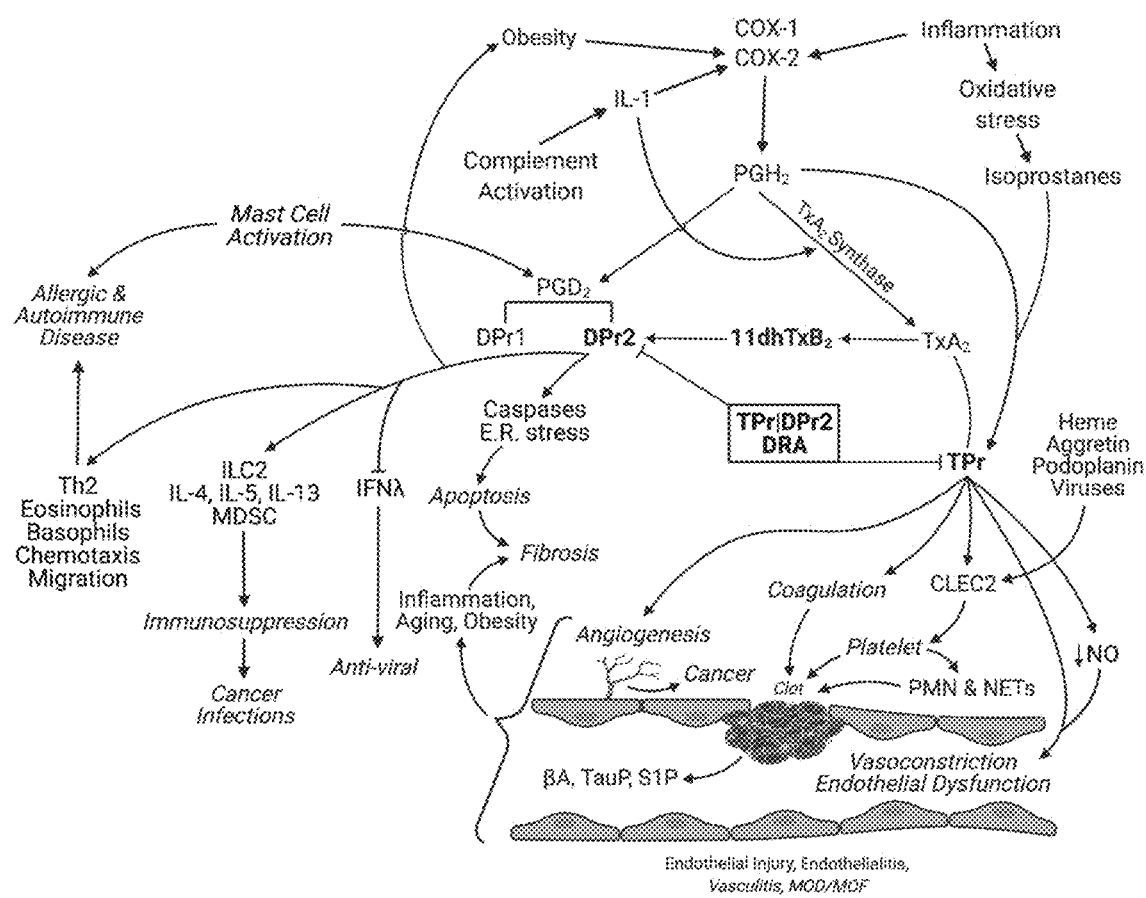

DUAL ANTAGONIST OF PGD$_2$/DPR2 AND THROMBOXANE A$_2$/TPR RECEPTORS AND USE FOR TREATMENT OF MALADAPTIVE IMMUNE RESPONSE OR THROMBOTIC DIATHESIS

This application is a continuation of International Patent Application No. PCT/IB2021/052693 filed on 31 Mar. 2021, which claims priority to U.S. Provisional Application No. 63/003,286 filed 31 Mar. 2020, 63/005,205 filed 3 Apr. 2020, 63/027,751 filed 20 May 2020 and 63/092,921 filed 16 Oct. 2020, the disclosure of which are incorporated herein by reference in its entirety.

FIELD OF THE INVENTION

This disclosure relates to treatment of various mammalian diseases and conditions related to direct and/or indirect activation of thromboxane and prostaglandin receptors using an effective dose of an agent that is a dual receptor antagonist (DRA) of PGD$_2$/DPr2 and thromboxane A$_2$/TPr receptor signaling. The disease conditions that are candidates for treatment with the DPr2|TPr dual receptor antagonist (TPr|DPr2 DRA) have underlying maladaptive or deficient immune responses or a thrombotic diathesis or both. The etiology of these disease conditions include infections; vascular injury; inflammation; aging; obesity; allergic and autoimmune diseases; platelet activation, coagulopathy, thrombosis, immunothrombosis and thromboinflammation; fibrosis; and neoplasia. The examples of such disease conditions include but are not limited to infections including community acquired pneumonia caused by viruses such as coronaviruses, influenza, respiratory syncytial viruses and sepsis; allergic, eosinophilic and mast cell disorders including eosinophilic esophagitis, mast cell activation syndrome, atopic disorders, allergic interstitial nephritis; cancers including prostate, kidney and leukemia; hemolytic disorders including sickle cell disease and thrombotic microangiopathy; neurological conditions including ischemia and infarction, Alzheimer's disease and Parkinson's disease; and vascular disorders with platelet activation including small, medium and large vessel vasculitis, pernio or chilblains. Buerger's disease, disseminated intravascular coagulopathy, arterial aneurysms, pulmonary arterial hypertension and hemodialysis vascular access malfunction.

BACKGROUND OF THE INVENTION

Inflammation is a common and important feature of a wide variety of human diseases and disorders including infective, metabolic, cardiovascular, hematologic, thrombotic, fibrotic, neurologic, cancer, immunologic, autoimmune, obesity and aging. Inflammation stimulates the inducible enzyme cyclooxygenase-2 (COX-2) present in all cells to unleash lipid mediators originating from arachidonic acid that include thromboxane A$_2$ (TxA$_2$) and prostaglandin D$_2$ (PGD$_2$).

Clinicians recognize that thromboxane A$_2$ stimulated thromboxane prostanoid receptor (TPr) activation leads to endothelial, platelet, and granulocyte activation and release of neutrophil extracellular traps (NETs). The vascular injury, vasculitis, thrombosis and thromboinflammation that ensue lead to ischemia reperfusion injury and are currently treated with antiplatelet agents and/or anticoagulants. It is known that thromboxane A$_2$ (TxA$_2$) mediates and contributes to various diseases such as bronchial asthma, ischemic heart disease, cerebrovascular disorders, fibrosis and cancer. A number of TxA$_2$ synthase inhibitors and TxA$_2$ receptor (TPr) antagonists have been developed to treat these diseases.

Likewise, clinicians recognize that PGD$_2$ binds at each of two G protein-coupled receptors: prostaglandin D$_2$ receptor 1 (DPr1) and prostaglandin D$_2$ receptor 2 (DPr2). PGD$_2$ activation of DPr1 receptors stimulates cyclic adenosine monophosphate (cAMP signaling) and leads to anti-inflammatory, immunomodulatory, anti-platelet, anti-fibrotic, and anti-chemotactic responses for eosinophils and basophils and thereby anti-allergic responses, and strengthens endothelial barrier function. PGD$_2$ activation of DPr2 (formerly known as CRTh2) receptors mediates polarization of the immune response from a T-helper cell Th1 to a T-helper cell Th2 immune response while mediating effects including pro-inflammatory, immunosuppressive via activation of ILC2 and MDSC cells and inhibition of the innate immune response, pro-fibrotic, pro-apoptotic via induction of ER stress, pro-chemotactic for eosinophils and basophils and thereby pro-allergic responses. This response commonly occurs in allergic rhinitis, asthma and in some viral infections, including respiratory syncytial virus, severe SARS-CoV-1, and severe SARS-CoV-2. The Th2 inflammatory responses are characterized by the recruitment and activation of mast cells, basophils, eosinophils, and goblet cells, as well as hyperplasia in airway and intestinal epithelia. Although these immune responses function as protective immunity against helminths invading cutaneous or mucosal sites, they are inappropriately activated in the conditions listed above, doing more harm than good. Furthermore. PGD$_2$/DPr2 signaling induces apoptosis in a variety of cli types, further aggravating tissue injury induced by activation of TxA$_2$/TPr signaling.

In 2004 Böhm et al. reported that thromboxane A$_2$ is unstable and is rapidly converted in vivo to a stable metabolite 11-dehydro-thromboxane-B$_2$ (11dhTxB$_2$). Although previously thought to be an inactive metabolite, 11dhTxB$_2$ acts as a full agonist of the DPr2 receptor [Böhm et al., *J Biol Chem.* (2004) doi:10.1074/jbc.M310270200] (FIG. 1). Therefore, patients with diseases as varied as diabetes, obesity, kidney failure, hypertension, atherosclerosis, sickle cell disease, rheumatoid arthritis, SARS-CoV-2, SARS-CoV-1, sepsis. Kawasaki disease, HIV, dengue infection, influenza, lymphocytic choriomeningitis virus, cancer, hepatitis C, type I herpes simplex virus, vaccinia, vesicular stomatitis virus, chikungunya virus, and Newcastle disease virus, which are characterized by high TxA$_2$ have an increased risk of developing maladaptive immune response and more severe complications through amplification of both TxA$_2$/TPr and PGD$_2$/DP2 signaling and TxA$_2$/TPr-PGD$_2$/DPr2 interactions mediated by 11dhTxB$_2$.

During training, clinicians may learn of the mechanisms of action that underlie inflammation, aging, obesity, cardiovascular disease, immune dysfunction, autoimmunity, infection, cancer and other diseases. In general, however, specialization follows general training, and the practitioner changes focus to diseases commonly associated with their specialty and the treatment of these disorders. As an example, while cardiologists have focused on TxA$_2$/TPr signaling, immunologists and allergists have focused on the antagonism of PGD$_2$/DPr2 signaling. Thus, the 2004 report by Böhm et al. has been largely ignored in clinical practice. Furthermore, in general, the scientists, pharmaceutically companies and drug developers have promoted the evolution from receptor antagonists that exhibit low selectivity to drugs that are selective for a single receptor. This change led to the development of selective DPr2 antagonists including fevipiprant, setipiprant, ADC-3680, AZD-1981, MK-1029.

MK-7246. OC459, OC000459, QAV-680, and TM30089; and selective TPr antagonists including Seratrodast (AA-2414), Terutroban (S18886), PTA$_2$. 13-APA, GR-32191, Sulotroban (BM-13177), SQ-29,548, SQ-28.668. ONO-3708. EP-045, BMS-180,291, and S-145.

This invention provides a solution to this long-felt shortcoming in integrating divergent signaling pathways mediating a particular disease (FIG. 1). As an example, in COVID-19, the inventor, using a single drug, namely ramatroban, targets both PGD$_2$/DPr2 and TxA$_2$/TPr signaling thereby having a single drug serve multiple benefits as an immunomodulator, anti-inflammatory and anti-thrombotic agent.

SUMMARY OF THE INVENTION

It is an aspect of the present invention to provide new methods for preventing and/or treating various disease states that are characterized by activation of both TxA$_2$/TPr and PGD$_2$/DPr2 signaling which may lead to mutual amplification of signaling by both the TxA$_2$/TPr and PGD$_2$/DPr2 pathways (FIG. 1). Dual activation of this type occurs as part of pathological conditions that include infections (community acquired pneumonia; sepsis, septic shock; viral infections including respiratory, cardiac, gastrointestinal and neurological infections; parasitic infections; and helminth infestations); metabolic diseases (diabetes, obesity, kidney failure and uremia); cardiovascular diseases (hypertension, atherosclerosis), hematologic diseases (sickle cell disease, paroxysmal nocturnal hemoglobinuria, thalassemia, microangiopathic hemolytic anemia), thrombotic disorders (thrombotic thrombocytopenic purpura, disseminated intravascular coagulopathy); cancer and paraneoplastic syndromes; allergic, immunologic and autoimmune diseases (allergic interstitial nephritis, SLE, rheumatoid arthritis, mast cell activation syndrome, eosinophilic disorders including eosinophilic esophagitis, ulcerative colitis, Crohn's disease), neurological diseases (Alzheimer's. Parkinson's, Dementia with Lewy bodies), renal diseases (lupus nephritis, acute kidney injury, collapsing focal segmental glomerulosclerosis, progression of acute to chronic kidney disease, rhabdomyolysis, cardiorenal syndrome, and hepatorenal syndrome), and snake bites.

It is one aspect of the present invention to provide a composition and method for preventing and/or treating hemolytic diseases, and further preventing and/or ameliorating exacerbations of the disease caused by inappropriate amplification of both TxA$_2$/TPr and PGD$_2$/DPr2 signaling, in specific embodiments, hemolytic diseases include, but are not limited to alpha thalassemia, beta thalassemia, sickle cell disease, paroxysmal nocturnal hemoglobinuria, and microangiopathic hemolytic anemia (MAHA). In certain aspects, the present invention provides a composition and method for preventing and/or treating sickle cell disease; and further preventing and/or ameliorating disease exacerbations (FIG. 2) In a specific embodiment, the disease exacerbation is vaso-occlusive crisis.

It is another aspect of the present invention to provide a composition and method for treating venomous snake bites; and further preventing and/or ameliorating exacerbations of the exposure to venom caused by inappropriate amplification of both TxA$_2$/TPr and PGD$_2$/DPr2 signaling. In a preferred embodiment, the snake bite is from the *Calloselasma rhodostoma* snake (also known as Malayan pit viper).

An aspect of the present invention is to provide a composition and method for preventing and/or treating kidney disease, and further preventing and/or ameliorating exacerbations of physiological responses to kidney failure caused by inappropriate amplification of both TxA$_2$/TPr and PGD$_2$/DPr2 signaling. In certain embodiments, kidney diseases include but are not limited to lupus nephritis, diabetic nephropathy, renal flares, reduced glomerular filtration rate, chronic kidney disease (CKD), tubulointerstitial fibrosis, focal segmental glomerular sclerosis (FSGS), collapsing FSGS, acute kidney injury (AKI), polycystic kidney disease (PKD), hepatorenal syndrome and cardiorenal syndrome. In specific preferred embodiments, the kidney disease is rhabdomyolysis-induced acute kidney injury, acute kidney injury (AKI) from non-specific cause, lupus nephritis, allergic interstitial nephritis, delayed allograft function, acute or chronic transplant rejection, and cardiorenal syndrome.

Another aspect of the present invention is to provide a composition and method for preventing and/or treating cardiovascular disease, and further preventing and/or ameliorating exacerbations associated with cardiovascular disorders caused by inappropriate amplification of both TxA$_2$/TPr and PGD$_2$/DPr2 signaling. In specific embodiments, cardiovascular diseases include essential hypertension, arteriosclerosis, hypertensive arterial sclerosis, malignant hypertension; primary and secondary pulmonary arterial hypertension; coronary artery aneurysms with or without Kawasaki disease; arterial aneurysms including aortic aneurysms; transthyretin amyloidosis, gangrene; calciphylaxis; calcific uremia arteriolopathy, frostbite; ischemia reperfusion injury of the heart; Takotsubo syndrome; cardiomyopathy; myocarditis; Takayasu arteritis; Moyamoya disease; vascular disease including stroke, silent cerebral infarcts, multi-infarct dementia, restenosis after coronary angioplasty, restenosis after coronary stent implantation, coronary stent thrombosis, saphenous vein graft failure; peripheral vascular disease, Buerger's disease. In certain embodiments, the vascular disease is Kawasaki disease, Moyamoya disease, Takotsubo syndrome, amyloid cardiomyopathy, and venous stenosis following creation of an AV fistula for hemodialysis.

In another aspect, the present invention provides a composition and method for preventing and/or treating thrombotic diseases, and further preventing and/or ameliorating exacerbations of thrombolytic disorders caused by inappropriate amplification of both TxA$_2$/TPr and PGD$_2$/DPr2 signaling. In specific embodiments, thrombotic diseases include, but are not limited to thrombotic microangiopathy (TMA), thrombotic thrombocytopenia purpura (TTP), hemolytic-uremic syndrome (HUS), disseminated intravascular coagulation (DIC), microangiopathic hemolytic anemia (MAHA), pulmonary embolism (PE), deep venous thrombosis (DVT), venous thromboembolism (VTE), and arterial thrombosis.

Figure 3:
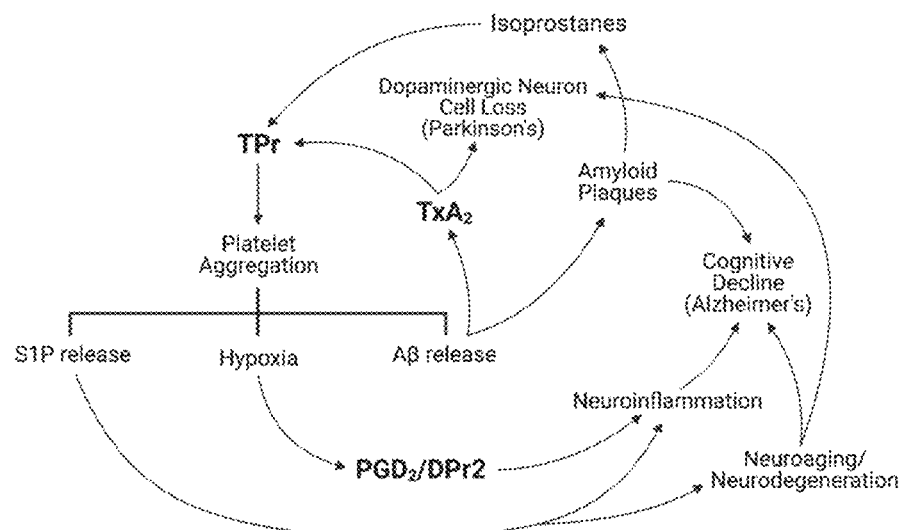

An aspect of the present invention provides a composition and method for preventing and/or treating neurological diseases, and further preventing and/or ameliorating disease exacerbations caused by inappropriate amplification of both TxA$_2$/TPr and PGD$_2$/DPr2 signaling. In certain embodiments, neurological diseases include but are not limited to Alzheimer's disease, Parkinson's disease, dementia with Lewy bodies, Gaucher's disease, Huntington's disease, transmissible spongiform encephalopathies or prion diseases, depression, sleep and behavior disorders, cerebral malaria, age related neurodegeneration, virus, bacteria, fungus, parasite and amoeba induced encephalitis, vascular dementia, thrombotic thrombocytopenia purpura induced confusion, post-sepsis syndrome including long-haul COVID and brain fog, multisystem inflammatory disease in children, amyotrophic lateral sclerosis, multi-infarct dementia, limbic-predominant age related TDP-43 encephalopathy (LATE), Zika induced microcephaly, amyloidosis, dialysis dementia, and/or chronic and acute neuroinflammation. In preferred embodiments, the neurological diseases are Alzheimer's and Parkinson's disease (FIG. 3).

An aspect of the present invention provides a composition and method for preventing and/or treating pain caused by inappropriate amplification of both $TxA_2$/TPr and $PGD_2$/DPr2 signaling, including but not limited to mechanical hyperalgesia, allodynia, heat hyperalgesia, cold hyperalgesia, deep-tissue/musculoskeletal hyperalgesia, and disease associated pain. A preferred embodiment of the present invention is to induce an analgesic effect in patients experiencing pain from a disease condition without causing addiction. A specific embodiment of the present invention is to prevent and/or treat pain crises in a patient with sickle cell disease (SCD) and induce an analgesic effect in patients experiencing pain without inducing the adverse effect of addiction. Another specific embodiment of the present invention is treatment of patients with painful diabetic neuropathy manifesting as cutaneous hypersensitivity or allodynia. Other specific embodiments of the present invention is the treatment of allodynia associated with Herpes infection, psoriatic arthritis, varicella-zoster virus infection, fibromyalgia, peripheral neuropathy, complex regional pain syndrome, autoimmune disease and Crohn's disease.

An aspect of the present invention provides a composition and method for preventing and/or treating amyloidosis; and further preventing and/or ameliorating exacerbations caused by inappropriate amplification of both $TxA_2$/TPr and $PGD_2$/DPr2 signaling. In certain embodiments, amyloid associated diseases include but are not limited to Amyloid A amyloidosis, transthyretin amyloidosis leading to cardiomyopathy referred to as Transthyretin Amyloid Cardiomyopathy (ATTR-CM), hereditary amyloidosis, wild-type amyloidosis or localized amyloidosis affecting the heart, lungs, liver, skin, kidneys, brain including Alzheimer's disease.

Another aspect of the present invention is to provide a composition and method for preventing and/or treating diseases associated with fibrosis, and further preventing and/or ameliorating exacerbations caused by inappropriate amplification of both $TxA_2$/TPr and $PGD_2$/DPr2 signaling. In certain embodiments, fibrosis-associated diseases include but are not limited to lung diseases (fibrothorax, pulmonary fibrosis including cystic fibrosis and idiopathic pulmonary fibrosis, silicosis, radiation-induced lung injury and pneumoconiosis); liver diseases (bridging fibrosis, cirrhosis, alcoholic liver disease, non-alcoholic fatty liver disease, non-alcoholic steatohepatitis, primary sclerosing cholangitis and non-cirrhotic hepatic fibrosis); heart diseases (right ventricular fibrosis, congestive heart failure, myocarditis and myocardial fibrosis including interstitial fibrosis and replacement fibrosis); brain dysfunctions (glial scarring, amylotrophic lateral sclerosis, scarring resulting from brain injuries including ischemic stroke, penetrating brain injuries, brain contusions, concussions, anoxic brain injuries, diffuse axonal injury, hypoxic brain injuries, multi-infarct dementia, arteriosclerotic dementia, vascular dementia of acute onset, subcortical vascular dementia, mixed cortical and subcortical vascular dementia); PERITONEUM: peritoneal fibrosis, encapsulating peritoneal sclerosis; KIDNEY: diabetic nephropathy, lupus nephritis, cyclosporine nephrotoxicity, renal allograft rejection, tubulointerstitial fibrosis, polycystic kidney disease, glomerulosclerosis, renal vasculitis including eosinophilic granulomatosis with polyangiitis or Churg-Strauss syndrome; SKIN: acne, blisters, hives, actinic keratosis, eczema, rosacea, latex allergy, psoriasis, contact dermatitis, vitiligo, warts, chickenpox, seborrheic eczema, keratosis pilaris, melasma, impetigo, fifth disease, perniosis, Raynaud's syndrome, rashes and burns, Dupuytren's contracture, keloid, OTHERS: Mediastinal fibrosis, retroperitoneal fibrosis, myelofibrosis, endometriosis, nephrogenic systemic fibrosis, progressive massive fibrosis, scleroderma/progressive systemic sclerosis (PSS), organ transplant rejection, preterm births, systemic lupus erythematosus and adhesive capsulitis.

An aspect of the present invention is to provide a composition and method for preventing and/or treating muscular dystrophy; and further preventing and/or ameliorating exacerbations caused by inappropriate amplification of both $TxA_2$/TPr and $PGD_2$/DPr2 signaling. In certain embodiments, muscular dystrophy include but are not limit to Duchenne muscle dystrophy, Becker muscular dystrophy and Limb-Girdle muscular dystrophy.

An aspect of the present invention is to provide a composition and method for preventing and/or treating bone diseases, and further preventing and/or ameliorating exacerbations caused by inappropriate amplification of both $TxA_2$/TPr and $PGD_2$/DPr2 signaling. In certain embodiments, bone disease includes but are not limited to bone marrow infarcts, avascular necrosis, adynamic bone disease and osteopetrosis.

Another aspect of the present invention is to provide a composition and method for preventing and/or treating diabetes mellitus and further preventing and/or ameliorating exacerbations caused by inappropriate amplification of both $TxA_2$/TPr and $PGD_2$/DPr2 signaling. In a specific embodiment, diabetes is type I diabetes. In another specific embodiment the disease complication is diabetic foot.

Another aspect of the present invention is to provide a composition and method for preventing and/or treating metabolic diseases and further preventing and/or ameliorating exacerbations caused by inappropriate amplification of both $TxA_2$/TPr and $PGD_2$/DPr2 signaling. In certain embodiments, metabolic diseases include but are not limited to obesity, insulin resistance and type 2 diabetes. In a specific embodiment, the metabolic disease is aspirin resistance.

Another aspect of the present invention is to provide a composition and method for preventing and/or treating Type 2 inflammatory diseases; and further preventing and/or ameliorating exacerbations caused by inappropriate amplification of both $TxA_2$/TPr and $PGD_2$/DPr2 signaling.

In certain embodiments, diseases driven by hyperactive type 2 immune responses include but are not limited to eosinophilic esophagitis, mast cell activation syndrome, chronic rhinosinusitis, acute promyelocytic leukemia, Churg-Strauss syndrome, drug allergies, allergic interstitial nephritis, allergic interstitial cardiomyopathy or acute interstitial myocarditis, chronic eosinophilic leukemia, eosinophilic peritonitis, graft eosinophilia in transplant organs and graft rejection, graft versus host disease, idiopathic hypereosinophilic syndrome, lymphatic filariases, Crohn's disease, mastocytosis, allergic interstitial nephritis, urticaria pigmentosa and anaphylaxis.

An aspect of the present invention is to provide a composition and method for preventing and/or treating autoimmune disease and further preventing and/or ameliorating exacerbations caused by inappropriate amplification of both $TxA_2$/TPr and $PGD_2$/DPr2 signaling. Certain embodiments of autoimmune diseases include but are not limit to rheumatoid arthritis, systemic lupus erythematosus, systemic sclerosis, multiple sclerosis. IgA nephropathy. IgA vasculitis, diabetes mellitus, ANCA vasculitis, myasthenia gravis, celiac disease, Sjögren's syndrome, polymyalgia rheumatica, autoimmune encephalitis, alopecia areata, small, medium and large vessel vasculitis. In preferred embodiments, the vasculitis disease is systemic lupus erythematosus and eosinophilic granulomatosis with polyangiitis or Churg-Strauss syndrome.

Another aspect of the present invention is to provide a composition and method for preventing and/or treating infections and further preventing and/or ameliorating exacerbations caused by inappropriate amplification of both $TxA_2/TPr$ and $PGD_2/DPr2$ signaling. In certain embodiments infections may include but are not limited to viral, fungal, bacterial, parasitic and amoebic infections. In specific embodiment, the infection is a viral infection wherein the virus is HIV, dengue virus, respiratory syncytial virus or a coronavirus (e.g., SARS-CoV-2, SARS, MERS). In another embodiment is a condition in which the innate immune response to the viral infection is blunted by failure of interferon lambda expression in response to the virus, allowing replication and propagation of the virus.

Another aspect of the present invention is to provide a composition and method for preventing infectious diseases by vaccination while concomitantly preventing and/or ameliorating exacerbations or complications caused by inappropriate amplification of both $TxA_2/TPr$ and $PGD_2/DPr2$ signaling. In certain embodiments vaccines may include but are not limited to influenza vaccine, HIV vaccine, hepatitis A, B or C vaccine, SARS-CoV-2 vaccine, pneumococcal vaccine, meningococcal vaccine, malaria vaccine, tetanus-diphtheria-pertussis vaccine, zoster vaccine. In certain embodiments the vaccine is administered by oral, nasal, subcutaneous, intramuscular or intravenous route in conjunction with the administration of a pharmaceutical composition comprising a dual receptor antagonist of DPr2 for prostaglandin $D_2$ and TPr for thromboxane $A_2$. In certain embodiments the dual receptor antagonist of DPr2 and TPr is ramatroban or its pharmaceutically acceptable salt or a derivative that is administered concurrently with vaccine.

An aspect of the present invention is to provide a composition and method for preventing and/or treating respiratory diseases and further preventing and/or ameliorating exacerbations caused by inappropriate amplification of both $TxA_2/TPr$ and $PGD_2/DPr2$ signaling. In certain embodiment, respiratory disease include but are not limited to acute lung injury, hospital-acquired pneumonia, acute respiratory distress syndrome, cystic fibrosis, acute asthma, emphysema, chronic pulmonary emphysema, chronic obstructive pulmonary disease, chronic bronchitis and/or smoking/smoking inducing lung injury and pneumoconiosis. In a preferred embodiment, the respiratory diseases are community-acquired pneumonia, and primary or secondary pulmonary hypertension.

Another aspect of the present invention is to provide a composition and method for preventing and/or treating cancer, cancer resistance and/or paraneoplastic syndromes; and further preventing and/or ameliorating exacerbations caused by inappropriate amplification of both $TxA_2/TPr$ and $PGD_2/DPr2$ signaling. In a specific embodiment the patient is receiving stem cell therapy and is experiencing inappropriate amplification of both $TxA_2/TPr$ and $PGD_2/DPr2$ signaling.

In accordance with each of the above aspects, the present invention provides for methods of preventing, reversing, ameliorating or treating each of the said diseases by administering a therapeutically effective amount of a dual receptor antagonist of both the $TxA_2/TPr$ and $PGD_2/DPr2$ receptors to a patient in need thereof. In a certain embodiments, the dual receptor antagonist of the $TxA_2/TPr$ and $PGD_2/DPr2$ receptors comprises a therapeutically effective amount of (3-[(3R)-3-[(4-fluorophenyl)sulfonylamino]-1,2,3,4-tetrahydrocarbazol-9-yl]propanoic acid) (ramatroban), and pharmaceutically acceptable salts thereof. In certain embodiments, the dual receptor antagonist of the $TxA_2/TPr$ and $PGD_2/DPr2$ receptors comprises a therapeutically effective amount of sodium salt 3-[(3R)-3-[(4-fluorophenyl)sulfonylamino]-1,2,3,4-tetrahydrocarbazol-9-yl]propanoate (ramatroban sodium) or a potassium, magnesium or calcium salt of ramatroban or ramatroban-based analog. In a certain embodiment, the ramatroban based analog contains a fluorine group. In certain embodiments the ramatroban analog is optimized for binding to the G-protein coupled receptor 44 (GPR44) or DPr2 which is highly beta cell-specific within the insulin-positive islets of Langerhans while retaining its antagonistic activity for TPr.

In any one of the methods described above and others described herein, the dual TPr|DPr2 antagonist is preferably administered in an amount effective to provide plasma concentrations from 1 nanomoles/L to 1000 nanomoles/L. In certain embodiments, the dual TPr|DPr2 antagonists are formulated for delivery by the oral, intranasal, aural, ocular, rectal, vaginal, sublingual, buccal, or parenteral routes, including peritoneal, transdermal, subcutaneous, intramuscular, intravenous and intrathecal routes.

BRIEF DESCRIPTION OF THE ACCOMPANYING DRAWINGS

FIG. 1: Shows mechanistic pathways that graphically illustrate biological pathways activated by inflammation or oxidative stress as well as exemplary diseases characterized by inflammation and/or oxidative stress. It also shows $PGD_2/DPr2$ axis suppresses the cell mediated immune response to pathogen via the ILC2-Interleukin 13-MDSC pathway. It further shows the mechanism of action of a dual inhibitor of both thromboxane $A_2$ and prostaglandin $D_2$ receptors (i.e., TPr|DPr2 DRAs) as disclosed herein target the amplification of thromboxane $A_2$ and $PGD_2/DP2$ signaling, including amplification that occurs indirectly through interactions mediated 11-dehydro-thromboxane $B_2$.

The abbreviations of FIG. 1 are COX, cyclooxygenase; PG, prostaglandin; $TxA_2$; thromboxane $A_2$; DPr1, D prostanoid receptor 1; TPr, thromboxane prostanoid receptor; DRA, dual receptor antagonist; Th2; T help 2; ILC2, type 2 innate lymphoid cells; IL, interleukin; MDSC, myeloid-derived suppressor cells; IFN, interferon; NO, nitric oxide; PMN, neutrophils; NETs, neutrophil extracellular traps; βA, Amyloid Beta; TauP, Tau proteins; S1P, sphingosine-1-phosphate; MOD, multiorgan dysfunction; MOF, multiorgan failure.

Figure 2:
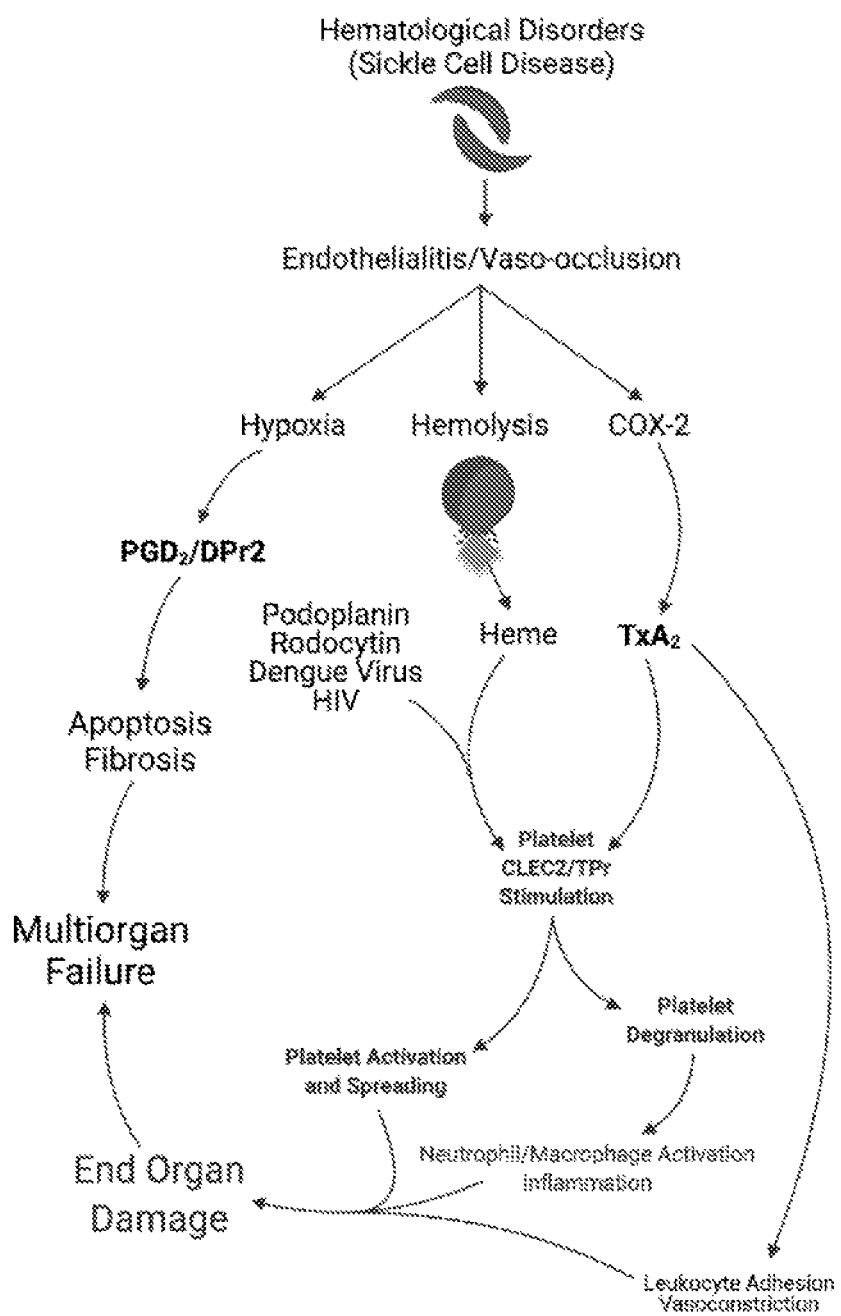

FIG. 2: Shows heme induced platelet activation mediated by CLEC2. It also shows TPr|DPr2 DRA inhibits the podoplanin-CLEC2-$TxA_2/TPr$ signaling thereby reducing peritoneal fibrosis, encapsulating peritoneal sclerosis and ultrafiltration failure.

FIG. 3: Shows TPr activation causes increased Aβ production through enhancement of APP mRNA stability. Therefore, TPr induced platelet activation risks development of Aβ and TauP related disorders including AD especially in patients with cardiovascular disease and high $TxA_2$. It also shows platelet aggregation by $TxA_2$ releases of sphingosine-1-phosphate (SIP).

Figure 4:
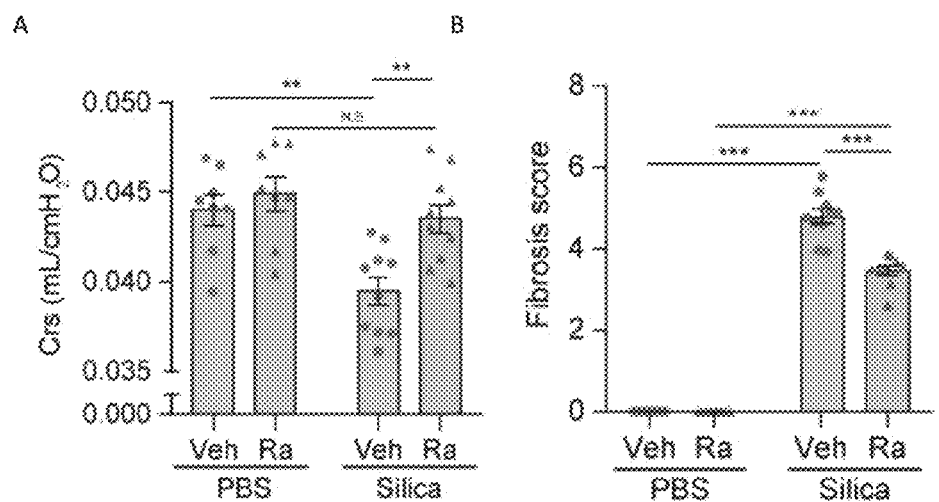

FIG. 4: Shows Ramatroban alleviated silica-induced pulmonary inflammation by inhibiting NLRP3 inflammasome, IL-beta and caspase-1, reducing infiltration with macrophages, lymphocytes and neutrophils; inhibiting fibrosis and resulting cardiopulmonary dysfunction while restoring lung compliance.

(A) Measurement of pulmonary function (compliance of the respiratory system) after treatment with vehicle or ramatroban in silicosis mice compared to controls.

(B) Fibrosis scores after treatment with vehicle or ramatroban in silicosis mice compared to controls.

DETAILED DESCRIPTION OF THE INVENTION

Reference will now be made in detail to representative embodiments of the invention. While the invention will be described in conjunction with the enumerated embodiments, it will be understood that the invention is not intended to be limited to those embodiments. On the contrary, the invention is intended to cover all clinically reasonable alternatives, modifications, and equivalents.

Unless defined otherwise, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

The term "TPr|DPr2 DRA" refers to a dual receptor antagonist of both the thromboxane $A_2$/TPr and prostaglandin D/DPr2 receptors. The term includes 3-[(3R)-3-[(4-fluorophenyl)sulfonylamino]-1,2,3,4-tetrahydrocarbazol-9-yl]propanoic acid (ramatroban), ramatroban sodium and their pharmaceutically acceptable derivatives and salts with 1-indolepropanoic acid structure. The term "ramatroban" also refers to dosage forms constituting generic equivalents to the drug.

Ramatroban's activity mainly resides on the (R)-enantiomer, which is from 10 to 100 times more active than its counterpart, (S)-enantiomer. (R)-enantiomer allows the administration of lower doses, minimizing the side effects and unspecific toxicities derived from the administration of the less active (S)-enantiomer. Therefore, the inventors propose enriching the pharmaceutical composition of a TPr|DPr2 DRA such as ramatroban with (R)-enantiomer dominating form for a more potent formulation allowing for the dose to be effectively reduced. In one embodiment the ratio of the (R)-enantiomer is enriched into the range from 50% to 100%. In one specific embodiment ramatroban, its salts and derivates used under this inventive concept are 100% composed of the (R)-enantiomer allowing maximum reduction in therapeutically effective dose.

The term an "effective amount" refers to the amount of the active agent that is required to confer the intended therapeutic effect in the subject. Effective amounts may vary, depending on the route of administration, formulation, and the health of the patient.

The term "treating" refers to administering the above-described TPr|DPr2 DRA compounds to a subject that has any of the described diseases, or has symptoms of said disease, or has a predisposition toward said disease, with the purpose to cure, heal, alleviate, relieve, alter, remedy, ameliorate, improve, or affect said disease, or the predisposition toward the said disease.

The term "$TxA_2$/TPr-11dh$TxB_2$-$PGD_2$/DPr2" refers to the crosstalk between $TxA_2$ and $PGD_2$/DPr2 pathways via the intermediate 11-dehydro-thromboxane $B_2$ in conjunction with $TxA_2$/TPr and $PGD_2$/Dpr2 signaling.

As used herein, the term "cancer" refers to the broad class of disorders characterized by hyperproliferative cell growth, either in vitro (e.g., transformed cells) or in vivo. Conditions which can be beneficially and uniquely treated or prevented by the compositions and methods of the invention include benign tumors and cancers that exhibit significant expression of TPr receptor for $TxA_2$ and DPr2 receptor for $PGD_2$ with or without significant expression of $TxA_2$ synthase or $PGD_2$ synthase. These cancers include but are not limited to gliomas in the brain or the spinal cord, melanoma, leukemias and cancers of colon, rectum, lung, kidneys, stomach, liver (hepatocellular carcinoma), thyroid, endometrium, pancreas, prostate, testis, breast, uterus, cervix and ovaries.

As used in this application, including the appended claims, the singular forms "a," "an," and "the" include plural references, unless the content clearly dictates otherwise, and are used interchangeably with "at least one" and "one or more."

As used in this application, the use of "or" means "and/or" unless stated otherwise. Furthermore, the use of the term "including." as well as other forms, such as "includes" and "included." is not limiting. Also, terms such as "element" or "component" encompass both elements and components comprising one unit and elements and components that comprise more than one subunit unless specifically stated otherwise.

As used herein, the term "about" represents an insignificant modification or variation of the numerical value such that the basic function of the item to which the numerical value relates is unchanged. Unless otherwise noted, technical terms are used according to conventional usage.

Unless otherwise indicated, all numbers expressing quantities of ingredients, reaction conditions, and so forth used in the specification and claims are to be understood as being modified in all instances by the term "about."

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

Unless otherwise explained, all technical, medical, and scientific terms used herein have the same meaning as commonly understood by one of ordinary skill in the art to which this disclosure belongs. The singular terms "a." "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description.

"Therapeutic" as used herein, includes treatment and/or prophylaxis. When used, therapeutic refers to humans as well as other animals. "Pharmaceutically or therapeutically effective dose or amount" refers to a dosage level sufficient to induce a desired biological result. That result may be the alleviation of the signs, symptoms or causes of a disease or any other alteration of a biological system that is desired. A "host" or "patient" is a living subject, human or animal, into which the compositions described herein are administered.

Further, ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise). Any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of" mean±20% of the indicated range, value, or structure, unless otherwise indicated. As used herein, the terms "include" and "comprise" are open ended and are used synonymously.

The present disclosure describes methods to prevent and treat diseases and conditions which are characterized by increased generation of thromboxane $A_2$ and have an increased risk of developing maladaptive immune response and more severe complications through amplification of both thromboxane $A_2$/TPr and $PGD_2$/DPr2 signaling and $TxA_2$/TPr-$PGD_2$/DPr2 interactions mediated by 11dhTxB$_2$. Mechanistic pathways that graphically illustrate biological pathways activated by inflammation or oxidative stress as well as exemplary diseases characterized by inflammation and/or oxidative stress are presented in FIG. 1. One major pathway begins with expression of cyclooxygenases 1 and 2, which induce expression of prostaglandin $H_2$. This intermediate serves as a substrate for enzymes that synthesize both thromboxane $A_2$ ($TxA_2$) and prostaglandin $D_2$ ($PGD_2$). Oxidative stress serves as a second cause for expression and elevation of $TxA_2$ but not $PGD_2$. However, the risk of activation of dual pathways of maladaptive immune response remains, since $TxA_2$ is unstable. Chronic exposure to high levels of $TxA_2$ results in conversion to 11dhTxB$_2$, an alternate agonist for the DPr2 receptor and $PGD_2$/DPr2 signaling that mediates maladaptive type 2 immune responses and inflammation.

The present disclosure describes methods to prevent and treat diseases and conditions which are characterized by increased generation of thromboxane $A_2$ with or without stimulation of $PGD_2$/DPr2 receptor signaling. The stimulation of $PGD_2$/DPr2 receptor signaling may be first, direct as a result of increased $PGD_2$ generation and increased expression of DPr2 receptors; or second, indirectly as a result of increased levels of 11dhTxB$_2$, a metabolite of $TxA_2$. This unifying thesis behind the inventive concept of this patent is the crosstalk between $TxA_2$ and $PGD_2$ signaling that allows a dual receptor antagonist to beneficially target the clinical consequences of such an interaction. These clinical consequences result from a multitude of underlying cellular cytokine and chemokine alterations which lead to (1) a maladaptive immune response characterized by a polarization from a Th1 to a Th2 response leading to the host mounting an immune response to a pathogen that is anti-helminthic in nature rather than anti-viral or anti-bacterial; (2) expansion of ILC2 and MDSC cells leading to an immunosuppressive state allowing microbes and tumor cells to thrive unaffected by the host immune response; (3) $TxA_2$/TPr signaling stimulates production of tissue factor which is highly prothrombotic and further leads to production of pro-inflammatory cytokines enhancing inflammation by activating protease-activated receptors on various cells. Amongst various inflammasome, the most notable is nucleotide-binding domain, leucine-rich-containing family, pyrin domain containing 3 (NLRP3) which strengthens a link between inflammation and coagulation in thrombosis. $TxA_2$/TPr induced inflammation and oxidative stress lead to formation of isoprostanes which in turn convert $PGD_2$ into isoprostane 15R-$PGD_2$, a largely selective DPr2 agonist (Cossette et al. *J Pharmacol Exp Ther*. (2007) doi: 10.1124/jpet.106.111062). This additional effect of $TxA_2$ facilitates amplification of $PGD_2$/DPr2 resulting in a maladaptive immune response as described above.

The dual receptor antagonists of this invention essentially target the lipid mediators, $TxA_2$ and $PGD_2$ generated in response to cyclooxygenase COX-2 stimulation. COX-2 is rapidly expressed in several cell types in response to growth factors, cytokines, and pro-inflammatory molecules and has emerged as the isoform primarily responsible for prostanoid production in acute and chronic inflammatory conditions. Mechanistic pathways that graphically illustrate biological pathways activated by COX-2 stimulation as well as exemplary diseases characterized by inflammation and/or oxidative stress are presented in FIG. 1. One major pathway begins with a specific agent such as a virus (e.g. SARS-CoV-2), aging, obesity, IL-1, complement activation and cancer leading to expression of COX-2, which generates prostaglandin $H_2$($PGH_2$) from arachidonic acid. This common intermediate, $PGH_2$, serves as a substrate for enzymes that synthesize both thromboxane $A_2$ ($TxA_2$) and prostaglandin $D_2$ ($PGD_2$). In addition to robust stimulation of COX-2 and $TxA_2$ by oxidative stress and inflammation, oxidative stress led generation of isoprostanes also amplifies selectively both TPr and DPr2 signaling as described above, while sparing the $PGD_2$/DPr1 axis. A potent and selective dual receptor antagonist of TPr and DPr2 that spares the DPr1 and other prostaglandin receptors is thereby able to antagonize the maladaptive immune response, thrombotic response and thromboinflammation without interrupting the anti-inflammatory and anti-thrombotic effects mediated by $PGD_2$/DPr1 and prostacyclin.

Cellular and Molecular Mechanism of Action of a Dual Receptor Antagonist of the Invention (FIGS. 1 and 2)

The mechanism of action of a dual inhibitor of both thromboxane $A_2$ and prostaglandin Da receptors (i.e., TPr|DPr2 DRAs) as disclosed herein target the amplification of thromboxane $A_2$ and $PGD_2$/DP2 signaling, including amplification that occurs indirectly through interactions mediated 11-dehydro-thromboxane $B_2$ (FIG. 1) and generation of isoprostane 15R-$PGD_2$, a largely selective DPr2 agonist to the exclusion of DPr1.

For example, a type 2 inflammatory immune response is critical for host resistance against helminthic worm infestations, but when inappropriately initiated or amplified causes atopic reactions that result in allergies, hypersensitivity and anaphylaxis. Type 2 immune response is characterized by release of pro-inflammatory cytokines including IL-4, IL-5 and IL-13 that recruit immune cells such as eosinophils, basophil and myeloid cells that play a role in many disease conditions, particularly, eosinophilic infiltration into organ systems. $PGD_2$/DPr2 signaling is one of the primary initiators of the type 2 immune response, including eosinophil recruitment (Zhang et al, Dis Esophagus, (2014) doi: 10.1111/dote.12118). Furthermore, another part of the type 2 immune response is the release of neutrophils extracellular traps (NETs) from neutrophils that trap pathogens like worms. Upon stimulation via CLEC2-TxA$_2$/TPr, platelets release mediators that activate neutrophils to release NETs (Sung et al. *Nature Communications*. (2019) doi: 10.1038/s41467-019-10360-4).

Thus, a dual receptor antagonist (DRA) of the invention acts as a potent TPr receptor antagonist. A DRA of the invention can also block the PGD$_2$ receptor, a chemoattractant receptor-homologous moiety expressed on Th2 cells (CRTh2 now referred to as DPr2). Since PGD$_2$ induces migration and degranulation of eosinophils through DPr2 receptors, blockage of DPr2 receptor by a DRA of the invention prevents eosinophil migration and degranulation and the late-phase inflammation and cell damage resulting therefrom (FIG. 1).

Many blood disorders including sickle cell disease (SCD) and hemolytic anemia lead to hemolysis of the red blood cells and subsequent release of cell-free hemoglobin. Under physiological conditions, free heme is scavenged by the plasma protein hemopexin (Joshua et al. *Haematologica*. (2020) doi:10.3324/haematol.2020.246488). Acute or chronic hemolysis exhausts this scavenging system for heme leading to an increase in free heme in the blood. Free heme is rapidly and spontaneously oxidized in the blood into ferric ($Fe^{3+}$) form, hemin. Hemin activates platelets by serving as a ligand for C-type-lectin-like receptor 2 (CLEC2) (FIG. 2). This indicates a role for platelet CLEC2 in platelet activation allowing progression of hematological disease. Cell-free heme also amplifies inflammation by activating inflammatory pathways including TLR signaling, neutrophil extracellular trap formation and priming of the inflammasome, consistent with the CLEC2 signaling pathway (Sung et al. *Nature*. (2019) doi: 10.1038/s41467-019-10360-4). Hemin has been implicated in the pathogenesis of acute chest syndrome, one of the leading causes of death in sickle cell disease. CLEC2 induced platelet aggregation activated by hemin is dependent on TxA$_2$/TPr signaling which was blocked by a TPr antagonist (Badolia et al. *J Biol Chem*. (2017) doi: 10.1074/jbc.M117.791012) (FIG. 2). Snake venom from the Malayan pit viper (*Calloselasma rhodostoma*) has been implicated in thrombosis. Snake venom protein rhodocytin is another mediator of platelet activation via activation of CLEC2 receptors (Sasaki et al. *J Thromb Haemost*. (2018) doi: 10.1111/jth.13987).

TPr|DPr2 Dual Receptor Antagonist for Prevention and Treatment of Cancer

Cancer is characterized by the excessive division of neoplastic cells that spread into surrounding tissue forming tumors. Tumor growth is often perpetuated by several factors mainly vascular remodeling (tumor cell nourishment) and immunosuppression (tumor cell evasion of immune response). Sprouting angiogenesis or blood vessel growth during cancer allows for tumor growth and metastasis. Vascular growth factors released by tumor cells mediate angiogenesis by releasing TxA$_2$ from endothelial cells which in turn, stimulates endothelial cell migration (Nie et al. *Biochem Biophys Res Commun*. (2000) doi: 10.1006/bbrc.1999.1840). Platelet activation mediated by TxA$_2$/TPr signaling also perpetuates tumor growth by masking the tumor cells from immune surveillance. Podoplanin is expressed in certain types of tumor cells, including squamous cell carcinomas, seminomas, and brain tumors (Susuki-Inoue. *Platelets*. (2018) doi: 10.1080/09537104.2018.1478401) implicating a role for CLEC2-TPr in the recruitment of platelets by the cancer. Immune response to cancer is also regulated by PGD$_2$/DPr2 axis and stimulation of the DPr2 receptor leads to immunosuppression, allowing the cancer to spread (Trabanelli et al. *Nat Commun*. (2017) doi: 10.1038/s41467-017-00678-2).

Glioma: COX-2, which is upstream of prostaglandin production including TxA$_2$ and PGD$_2$ plays a role in glioma invasion, angiogenesis and immunosuppression, and COX-2 inhibitors enhance the effects of conventional chemo- and radio-therapies against glioma cells. COX-2 downstream signaling pathways produce alternative targets for gliomas (Qiu et al. *Drug Discov Today*. (2017) doi: 10.1016/j.drudis.2016.09.017). In the treatment of glioma, inhibition of TxA$_2$ production induced tumor cell death of cancerous glioma cells with proapoptotic, antiproliferative and antiangiogenic effects in glioma. Inhibition of TxA$_2$ production also improved survival time of glioma mice and improved the efficacy of conventional alkylation chemotherapy in vivo (Schmidt et al. *Transl Oncol*. (2010) doi: 10.1593/tlo.09238). The immunosuppressive axis of PGD$_2$/DPr2 likely plays a role in glioblastoma as well since PGD$_2$ is the most abundant prostaglandin in the brain and is further increased during glioma.

Similar to glioma, TxA$_2$/TP and PGD$_2$/DPr2 signaling plays a role in kidney, thyroid, lung, colorectal, head and neck, stomach, liver, pancreatic, endometrial, urothelial, prostate, testicular, breast, cervical, ovarian, and skin (melanoma) cancers (see Table 1). In accordance with the above objects and others, the present invention is directed in part to a method of preventing, treating or ameliorating cancer in a subject in need of treatment thereof, comprising administering a therapeutically effective amount of a TPr|DPr2 DRA to the patient.

TABLE 1

Role of thromboxane A$_2$/TPr and PGD$_2$/DPr2 signaling in various cancers; and role of the dual receptor antagonist of DPr$_2$ and TPr in the treatment of cancer

| Cancer | Lipocalin PGD$_2$ synthase | Hematopoietic PGD$_2$ synthase | DP1 receptor | DP2 (CRTH2) receptor | TxA$_2$ synthase | TP receptor |
|---|---|---|---|---|---|---|
| Renal | + | + | + | NS | ++ | + |
|  | 2.2 | 0.8 | 0.3 | 0.1 | 4 | 1.8 |
| Glioma | ++ | + | NS | + | ++ | + |
|  | 54.3 | 3 | 0 | 0.4 | 4.9 | 1.7 |
| Thyroid | + | + | NS | NS | + | + |
|  | 2.8 | 0.9 | 0.1 | 0 | 1 | 1.3 |
| Lung | + | ++ | + | NS | + | + |
|  | 14.7 | 0.9 | 0.2 | 0.1 | 3.2 | 0.8 |
| Colorectal | + | NS | + | + | ++ | + |
|  | 4.4 | 0.3 | 0.2 | 0.4 | 4.5 | 0.6 |
| Head and Neck | + | NS | NS | NS | + | + |
|  | 2.8 | 0.4 | 0.2 | 0 | 1.2 | 0.5 |
| Stomach | + | + | + | + | + | + |
|  | 10.2 | 0.5 | 0.2 | 0.4 | 2.5 | 1.3 |
| Liver | + | NS | NS | + | + | + |
|  | 3.4 | 0.2 | 0.1 | 0.4 | 0.8 | 0.8 |
| Pancreatic | ++ | + | + | + | ++ | + |
|  | 26.1 | 1.7 | 0.2 | 0.4 | 5.1 | 1.1 |
| Endometrial | ++ | NS | NS | NS | + | + |
|  | 23.5 | 0.3 | 0.1 | 0.1 | 1.6 | 0.6 |
| Urothelial | + | NS | NS | NS | + | + |
|  | 5.4 | 0.3 | 0.1 | 0.1 | 0.9 | 0.6 |
| Prostate | ++ | NS | NS | NS | + | + |
|  | 48.5 | 0.7 | 0.1 | 0.1 | 3 | 0.5 |
| Testis | ++ | NS | + | NS | + | + |
|  | 23.9 | 0.1 | 0.2 | 0.1 | 1.5 | 1.4 |

TABLE 1-continued

Role of thromboxane A$_2$/TPr and PGD$_2$/DPr2 signaling in various cancers; and role of the dual receptor antagonist of DPr$_2$ and TPr in the treatment of cancer

| Cancer | Lipocalin PGD$_2$ synthase | Hematopoietic PGD$_2$ synthase | DP1 receptor | DP2 (CRTH2) receptor | TxA$_2$ synthase | TP receptor |
|---|---|---|---|---|---|---|
| Breast | + | ++ | + | NS | + | + |
|  | 4 | 1.2 | 0.2 | 0.1 | n | 0.9 |
| Cervical | + | NS | NS | NS | + | + |
|  | 6.6 | 0.4 | 0.1 | 0 | 1.1 | 0.4 |
| Ovarian | ++ | + | NS | NS | + | + |
|  | 42.1 | 0.6 | 0.1 | 0.1 | 1.2 | 0.7 |
| Melanoma | + | NS | NS | NS | + | ++ |
|  | 10 | 0.3 | 0 | 0.1 | 1.4 | 1.1 |

FPKM: Filaments per Kilobase Million; NS, not significant; +, slight increase; ++, significantly increased; NA; information not available (Data retrieved from The Human Protein Atlas)

Inappropriate hyperactivation of coagulation and platelet aggregation referred to a thrombotic or clotting disorder contributes to obstructed blood flow and organ damage. Many of these disorders are likely caused by excessive release of TxA$_2$ from damaged blood vessel wall leading to platelet aggregation. Furthermore, obstruction of arteries deprives organs of oxygen causing hypoxia. Hypoxia increases PGD$_2$ in the organs (Taniguchi et al. *J Neurosci*, (2007) doi: 10.1523/JNEUROSCI.0321-07.2007), increasing the risk of cell death and apoptosis due to the pro-inflammatory and pro-fibrotic role of PGD$_2$/DPr2.

In another embodiment of the present invention, TPr|DPr2 DRA are used to prevent or treat Thrombotic microangiopathies (TMAs), such as thrombotic thrombocytopenic purpura (TTP) and complement-mediated hemolytic uremic syndrome (HUS): These are characterized by platelet-rich microthrombi without significant fibrin clot formation or consumption coagulopathy. Thus, other TMAs generally present with thrombocytopenia and normal coagulation studies. In some cases, other TMAs are caused by clearly defined endothelial defects: TTP is caused by deficiency of the ADAMTS13 protease, which results in accumulation of very long von Willebrand factor multimers on the endothelial surface that are capable of binding platelets; Complement-mediated HUS is thought to be caused by complement-induced damage to the endothelium. These endothelial defects promote platelet adherence and activation without exposing the blood to large amounts of procoagulant substances. Since platelet activation and endothelial cell-platelet interaction also play a central role in all forms of TMA, a TPr|DPr2 DRA such as ramatroban is likely to be effective in treating all forms of the disease.

In another embodiment, the present invention describes methods for preventing or treating diffuse hypercoagulable state and diffuse endothelial activation or panendothelitis, common pathogenetic mechanisms in DIC, MODS, SIRS. The method comprises administering to a patient in need thereof an effective amount of a TPr|DPr2 DRA such as ramatroban.

In yet another embodiment, the present invention describes methods for preventing or treating hypercoagulable states, either idiopathic or secondary e.g. in infections and autoimmune diseases as described above. The method comprises administering to a patient in need thereof a TPr|DPr2 DRA such as ramatroban.

TPr|DPr2 Dual Receptor Antagonist for Prevention and Treatment of Autoimmune Diseases and Vasculitides Vasculitis is an inflammatory process that affects the vessel wall as the primary site of inflammation with presence of inflammatory leukocytes in vessel walls with reactive damage to mural structures. This process causes damage to the vessel wall and fibrinoid necrosis, it leads to the narrowing of the lumen due to thickening or to total occlusion due to thrombosis resulting in downstream tissue ischemia and necrosis. Moreover, the focal lesions within the vessel wall may also cause weakening with the subsequent development of aneurysms and/or rupture with bleeding into surrounding tissues.

Vasculitic syndromes are heterogeneous disorders whose disease manifestations may arise from the involvement of different types and sizes of blood vessels (i.e., small, medium, and large vessels) in different organs and systems. When only one organ is affected by the vasculitic process, it is regarded as a single-organ vasculitis (SOV) while the involvement of several organs and systems characterizes a systemic vasculitis. Systemic vasculitis can be primary when no etiological factor is identified or secondary to infections (e.g., secondary to hepatitis C or HIV infection), drug-induced (e.g., propylthiouracil, hydralazine), drug abuse (e.g., levamisole-induced vasculitis), systemic autoimmune diseases (e.g., systemic lupus erythematosus, rheumatoid arthritis, and Sjögren's syndrome), or to cancer. The exact pathogenetic mechanisms underlying these diseases are unknown.

During the acute and subacute phases of Kawasaki syndrome, both platelet count and tendency to aggregate increase with marked elevation in plasma level of thromboxane B$_2$ (TxB$_2$), a TxA$_2$ metabolite, and reduction in 6-keto-prostaglandin F1α (PGF$_{1\alpha}$), a prostacyclin metabolite, during the acute phase, followed by partial suppression of TxB$_2$ with therapy but almost undetectable PGF$_{1\alpha}$ levels for a long time after the disease. In addition, markers of endothelial stimulation or damage such as von Willebrand factor, thrombin-antithrombin III complex, tissue factor, and soluble thrombomodulin are increased. Further, presence of aneurysms induces stagnation of blood flow, facilitating spontaneous intravascular coagulation. TxA$_2$ regulates vascular tone via its inhibitory effect on the expression of inducible nitric oxide. Therefore, a TPr|DPr2 DRA antagonist would increase nitric oxide and vasorelaxation with improvement in coronary blood flow. Small veins and venules have an important role in determining the amount of blood flow returning to the heart and also capillary functions. TxA$_2$ antagonism with ramatroban will augment venular flow and capillary function.

In one embodiment. TPr|DPr2 DRA is used to treat small-, medium-, large- and variable-vessel vasculitis. In specific embodiments, vasculitis includes but are not limited to Takayasu arteritis, giant cell arteritis, polyarteritis nodosa. Kawasaki disease, multisystem inflammatory syndrome in children, ANCA-associated vasculitis, microscopic polyangiitis, granulomatosis with polyangiitis, soinophilic granulomatosis with polyangiitis (Churg-Strauss), immune complex small-vessel vasculitis, anti-glomerular basement membrane disease, cryoglobulinemic vasculitis, IgA vasculitis, hypocomplementemic urticarial vasculitis (anto-C1q vasculitis). Bahçet syndrome. Coggan's syndrome, single-organ vasculitis, primary central nervous system vasculitis, vasculitis associated with systemic disease and vasculitis associated with probable etiology.

Autoimmune Diseases

Platelet activation plays a major role in various autoimmune diseases (Habets et al. *Eur J Clin Invest*. (2013) doi: 10.1111/eci.12101), implicating a role for TxA$_2$. Dysregulation of immune responses by $PGD_2$ contributes to autoimmune disease including systemic lupus erythematosus (Pellefigues et al. *Nature Communications.* (2018) doi: 10.1038/s41467-018-03129-8). $TxA_2$/TPr-11dhTxB$_2$-$PGD_2$/DPr2 interactions may play a critical role in autoimmune diseases including rheumatoid arthritis, systemic lupus erythematosus, systemic sclerosis, multiple sclerosis. IgA nephropathy, IgA vasculitis, diabetes mellitus, myasthenia gravis, celiac disease, Sjögren's syndrome, polymyalgia rheumatica, alopecia, Castleman's diseases, juvenile idiopathic arthritis, psoriasis, polymyositis, relapsing polychondritis, adult-onset Still's disease, polymyalgia rheumatica, remitting seronegative symmetrical synovitis with pitting edema, uveitis, spondyloarthritis, periodic fever, familial mediterranean fever and aphthous stomatitis.

In accordance with the above objects and others, the present invention is directed in part to a method of preventing, treating or ameliorating autoimmune diseases in a subject in need of treatment thereof, comprising administering a therapeutically effective amount of a TPr|DPr2 DRA to the patient.

TPr|DPr2 Dual Receptor Antagonist for Prevention and Treatment of Endothelial Dysfunction and Cardiovascular Disease In addition to mediating platelet activation, $TxA_2$ is a potent vasoconstrictor and reduces nitric oxide, a critical vasodilator (Yamada et al. Circulation. (2003) doi: 10.1161/01.cir.0000093194.21109.ec). Vasoconstriction with $TxA_2$ contributes to hypertension and cardiovascular risk, especially in the elderly who have higher $TxA_2$ levels (Chiba et al. *Prostaglandins Leukot Med.* 1984) doi: 10.1016/0262-1746(84)90191-4). Furthermore, $TxA_2$ stimulates growth of vascular smooth muscle cells in the blood vessel wall, accounting for the vascular hypertrophy during hypertension.

$PGD_2$ is also involved in eosinophil accumulation and eosinophilia (Zhang et al. Diseases of the Esophagus. (2014) doi: 10.1111/dote.12118) Eosinophilia plays a role in vascular complications in a variety of disease, such as increasing the risk of coronary artery aneurysm in Kawasaki disease.

Ramatroban, a TPr|DPr2 DRA is 100 times more potent than aspirin in inhibiting platelet activation (Kariyazono et al. *Blood Coagul Fibrinolysis.* (2004) doi: 10.1097/00001721-200403000-00007). TPr|DPr2 DRA has shown efficacy in allergic rhinitis, atherosclerosis, coronary artery disease, myocardial infarction, splanchnic artery occlusion shock and sepsis (Ishizuka et al. *Cardiovasc Drug Rev.* (2004) doi: 10.1111/j.1527-3466.2004.tb00132.x). TPr|DPr2 DRA will also reduce cardiovascular risk in diseases including but not limit to pulmonary arterial hypertension, malignant hypertension, coronary artery aneurysm with or without Kawasaki disease, arterial aneurysms including aortic aneurysms, gangrene, calciphylaxis, frostbite, ischemia reperfusion injury, saphenous vein graft failure, hypertensive arterial sclerosis, Takotsubo syndrome, cardiomyopathy, myocarditis. Takayasu arteritis, moyamoya disease, peripheral vascular disease, stroke, silent cerebral infarcts, multi-infarct dementia, restenosis after coronary angioplasty, restenosis after coronary stent implantation, coronary stent thrombosis. In certain embodiments, the vascular disease is Kawasaki disease, Moyamoya disease. Takotsubo syndrome, amyloid cardiomyopathy, and venous stenosis following creation of an AV fistula for hemodialysis.

TPr|DPr2 Dual Receptor Antagonist for Prevention and Treatment of Pernio or Chilblains Pernio (also known as chilblains or perniosis) is a condition characterized by the development of cold-induced erythrocyanotic skin lesions. The word "chilblains" may be derived from the Old English words "chill" and "blegen" (sore). Pernio manifests as erythematous to violaceous macules, papules, plaques, or nodules in sites of cold exposure. The most common sites for involvement are the fingers and toes. Symptoms of pruritus, pain, or burning often accompany the skin lesions, and complications of blistering, ulceration, or secondary infection can occur. In many patients, pernio presents as an acute eruption that begins 12 to 24 hours after cold exposure and resolves within a few weeks. However, pernio may also follow a chronic or recurrent course. Treatment primarily involves protection of affected areas from cold environments. Pernio is distinct from lupus pernio, a form of cutaneous sarcoidosis. The pathogenesis of pernio is unclear. It is postulated that pernio results from an abnormal vascular response to cold exposure. Cold-induced vasoconstriction or vasospasm resulting in hypoxemia that stimulates an inflammatory response is a potential mechanism for the formation of skin lesions. A role for hyperviscosity or endothelial damage in the microvasculature associated with the presence of autoantibodies also has been considered. In one embodiment, TPr|DPr2 DRA is used to treat pernio and chilblains.

In accordance with the above objects and others, the present invention is directed in part to a method of preventing, treating or ameliorating pernio or chilblains in a subject in need of treatment thereof, comprising administering a therapeutically effective amount of a TPr|DPr2 DRA to the patient.

TPr|DPr2 Dual Receptor Antagonist for the Treatment of Buerger's Disease (Thromboangiitis Obliterans), *Cannabis* Arteritis and Tobacco Related Thromboangiitis Obliterans Thromboangiitis obliterans (TAO), also called Buerger's disease, is a nonatherosclerotic, segmental, inflammatory disease that most commonly affects the small to medium-sized arteries and veins of the extremities (upper and lower). Thromboangiitis obliterans is characterized by highly cellular and inflammatory occlusive thrombus with relative sparing of the blood vessel wall. Patients are young smokers who present with distal extremity ischemia, ischemic digit ulcers, or digit gangrene. The disease is strongly associated with the use of tobacco products, and smoking cessation is important to decrease the risk for amputation. *Cannabis* arteritis is clinically and pathologically indistinguishable from thromboangiitis obliterans but occurs less commonly compared with tobacco-related thromboangiitis obliterans. Thromboangiitis obliterans typically presents in young smokers less than 45 years of age. Vascular involvement in thromboangiitis obliterans usually begins with the distal arteries and veins, followed by more proximal arterial occlusive disease. Two or more extremities are usually involved. A seasonal variation has also been reported with patients more likely to present in the winter.

Thromboangiitis obliterans is a segmental inflammatory, nonatherosclerotic, occlusive vascular disease that affects the small and medium-sized arteries and veins of the upper and lower extremities. Histologically, the condition is distinguished from other forms of vasculitis by a highly cellular, inflammatory intraluminal thrombus with relative sparing of the vessel wall and, more specifically, sparing of the internal elastic lamina. Although the disease was recognized and the pathology described over 100 years ago, its pathogenesis is poorly understood. In the acute phase, inflammatory thrombi develop in the arteries and veins, typically of the distal extremities. The thrombus is occlusive, and polymorphonuclear leukocytes, microabscesses, and multinucleated giant cells may be present, but there is no evidence of fibrinoid necrosis. Although the external elastic lamina may show some disruption, the internal elastic lamina is intact. The intermediate (subacute) phase is characterized by progressive organization of the thrombus in the small to medium-sized arteries and veins. A prominent inflammatory infiltrate is still present within the thrombus but is less in the vessel wall. In the chronic phase, inflammation is no longer present and only organized thrombus and vascular fibrosis remain. The pathological appearance in the chronic phase is indistinguishable from all other types of occlusive arterial disease.

Endothelial dysfunction is involved in the pathogenesis of thromboangiitis obliterans. High titers of anti-endothelial antibodies have been detected. Vascular invasion of the tunica intima and also the tunica media is clearly demonstrated in affected vessels using endothelial cell-specific antigens. Endothelium-dependent vasodilation is also impaired in angiographically normal limbs in TAO patients. The presence of anticardiolipin antibodies is associated with an increased risk and severity of disease. Prothrombotic factors may also play a role in the pathogenesis of TAO. A TPr|DPr2 DRA will inhibit the endothelial activation, platelet activation; and endothelial-platelet and platelet-platelet interactions thereby serving as a treatment of the disease.

In accordance with the above objects and others, the present invention is directed in part to a method of preventing, treating or ameliorating thromboangiitis obliterans in a subject in need of treatment thereof, comprising administering a therapeutically effective amount of a TPr|DPr2 DRA to the patient TPr|DPr2 Dual Receptor Antagonist for Prevention and Treatment of Neurological Diseases Eicosanoids $TxA_2$ and $PGD_2$ play a key role in the pathogenesis of neurodegenerative disorders by mediating platelet activation (described above) and neuroinflammation, respectively. Administration of a TPr|DPr2 DRA including ramatroban and its derivatives can be used for prevention, slowing the progression and treatment of these brain disorders.

Alzheimer's Disease

A hallmark of Alzheimer's disease (AD) brain is the deposition of Tau protein (TauP) and senile plaques comprising amyloid β (Aβ) peptides that are derived from the amyloid precursor protein (APP). The plaque-containing AD brain undergoes oxidative stress leading to release of oxidized mediators that activate the TPr. TPr activation causes increased Aβ production through enhancement of APP mRNA stability (FIG. 3). Moreover, TPr antagonists have been shown to block these increases of Aβ secretion and decrease plaque formation (Cimetiere et al. *Bioorg Med Chem Lett*. (1998) doi: 10.1016/s0960-894x(98)00220-0) Thus, a TPr|DPr2 DRA will prevent AD development.

Platelets are the primary source (~90%) of Aβ peptide in human blood, while the Aβ peptide variants secreted by platelets are similar to those found in the senile plaques of AD patients (Kucheryavykh et al. *Int J Mol Sci*. (2018) doi: 10.3390/ijms19061705). This is consistent with presence of Aβ in the skin after blood clotting. Platelets also release Tau proteins, another diagnostic tool of AD (Mukaetova-Ladinska et al. *Curr Alzheimer Res*. (2018) doi: 10.2174/1567205015666180404165915). Therefore. TPr induced platelet activation risks development of Aβ and TauP related disorders including AD especially in patients with cardio-vascular disease and high $TxA_2$ (FIG. 3). Aβ is also involved in AA amyloidosis, hereditary amyloidosis, wild-type amyloidosis or localized amyloidosis affecting the heart, lungs, liver, skin, kidneys, brain and/or other organs which will be ameliorated with a TPr|DPr2 DRA (FIG. 3).

GV-971 (sodium oligomannate) is a multi-targeting oligosaccharide drug that improves cognitive impairment in Alzheimer's disease and would provide a strategy to treat neurological disorders including Alzheimer's disease in combination with a TPr|DPr2 DRA.

Parkinson's Disease $TxA_2$ induces release of AD peptides that in turn, upregulate $TxA_2$ in the brain, thus impairing motor function and causing Parkinson's like features (Yagami et al. Neurobiol Dis. (2004) doi: 10.1016/j.nbd.2004.04.013. $TxA_2$ leads to neuronal cell loss of dopaminergic neurons, a characteristic feature of Parkinson's disease. Consequently, both stroke and traumatic brain injury with high platelet activation and $TxA_2$ increase the long-term risk for Parkinson's disease.

In addition to Aβ peptides, platelet aggregation by $TxA_2$ releases of sphingosine-1-phosphate (SIP). 60% of patients with Parkinson's have seborrheic dermatitis characterized by "oily skin" and excess sebum secreted by the sebaceous gland (Sinclair et al. *nature communications*. (2021) doi: 10.1038/s41467-021-21669-4). Sebum from Parkinson's disease patients exhibit marked increases in sphingolipids and arachidonic acid metabolites, leading to production of sphingosine-1-phosphate (SIP) and $TxA_2$, respectively. S1P release is exacerbated by platelet activation while a TPr|DPr2 DRA is 150-fold more potent than aspirin inhibiting SIP release (Ulrych et al. JTH. (2011) doi: 10.1111/j.1538-7836.2011.04194.x) (FIG. 3). A TPr|DPr2 DRA provides a method of treating diseases with SIP involvement including but not limited to cancer, retinal inflammation, diabetic neuropathic, macular degeneration, sepsis, atherosclerosis, obstructive coronary artery disease, asthma and allergy, dermal aging, anaphylaxis, COPD, bronchitis, emphysema, myocardial infarction, obstructive coronary artery disease, ischemia/reperfusion injury, heart rate. Atopic dermatitis, acne vulgaris, lupus erythematosus, psoriasis, rheumatoid arthritis, osteoporosis, obesity, gastric cancer, diabetes, insulin resistance, hepatitis, deafness. Alzheimer's disease, Parkinson's disease, amyotrophic lateral sclerosis, Huntington's disease, multiple sclerosis, seborrheic dermatitis, ulcerative colitis, Crohn's disease, and/or alopecia areata.

An embodiment of the present invention is the prevention/treatment of neurodegeneration mediated by neurotropic infectious agents including retroviruses (HIV and human T lymphotropic virus type 1), Herpes group (HSV, CMV, Epstein-Barr virus, human herpesvirus 6. B virus), enteroviruses (Polioviruses, Coxsackieviruses, echoviruses), arboviruses, rabies virus, mumps virus, lymphocytic choriomeningitis virus, measles virus, rubella virus, nipah virus, JC virus, bacterial infections mediated by *Mycobacterium tuberculosis. Treponema pallidum, Borrelia burgdorferi*, Nocaria *asteroides*, Lpetospirm *Brucella, Rickettsia, Mycoplasma*, and *Ehrlichia*, parasitic infections mediated by Cysticercus, Txophasma *gondii*, Trypanosomo, Entamoeba *histolytica*, free-living amoebas, *Echinococcus, Schistcosoma, Angiostrongylus* cantonesis, and *Gnathostoma* spirinigerum, fungal infections including *Cryptococcus neoformans, Coccidioides immitis. Histoplasma capsulatum, Blastomyces dermatitidis, Candida*, Zygomycetes, *Aspergillus*, and *Sporothrix Schenckii* with a TPr|DPr2 DRA in combination with other neurological therapeutics.

Neuroinflammation

Neuroinflammation mediates the development of neurological diseases including Alzheimer's and Parkinson's and $PGD_2$ plays a key role. $PGD_2$ is increased in the brain 90-fold during hypoxia which may be caused by $TxA_2$ induced blood clotting and blood flow obstruction (Taniguchi et al. *J Neurosci.* (2007) doi: 10.1523/jneurosci.0321-07.2007) (FIG. 3). $PGD_2$ is metabolized to $PGJ_2$, which also stimulates DPr2. $PGJ_2$ is associated with Parkinson's disease-like pathology. A vicious cycle of $PGD_2$/$PGJ_2$/COX-2/$PGD_2$ promotes the transition from acute to chronic neuroinflammation that is involved in the development of diseases including Parkinson's (Corwin et al. *J Neuroinflammation.* (2018) doi: 10.1186/s12974-018-1305-3). A TPr/DPr2 DRA will not only block the proinflammatory effects of $PGD_2$, but also $PGJ_2$ induced neuroinflammation in the brain.

In accordance with the above objects and others, the present invention is directed in part to a method of preventing, treating or ameliorating neurological diseases in a subject in need of treatment thereof, comprising administering a therapeutically effective amount of a TPr|DPr2 DRA to the patient.

Emotional Impairment Induced by Pregnancy and Sicknesses Including Infections and Cancer Infectious and autoimmune diseases, diabetes, and tumors result in systemic inflammation, evoking a number of responses including fatigue, fever, anorexia, depression, and apathy, which are collectively known as sickness behavior. Depression, social withdrawal, loss of interest, and cognitive difficulties are accompanying symptoms in tumor patients. Upregulation of COX-2 and prostaglandin production in brain endothelial and perivascular cells, results in activation of neighboring neurons and these pathways are responsible for the behavioral changes observed in animal models of sickness behavior. $PGD_2$/DPr2 signaling plays a key role in sickness behavior. In accordance with the above objects and others, the present invention is directed in part to a method of preventing, treating or ameliorating psychological and psychiatric diseases in a subject in need of treatment thereof, comprising administering a therapeutically effective amount of a TPr|DPr2 DRA to the patient.

Pain

Arachidonic acid derived prostaglandins including $PGD_2$ and $TxA_2$ not only contribute to the development of inflammation as intercellular pro-inflammatory mediators but also promote the excitability of the peripheral somatosensory system, contributing to pain exacerbations. Peripheral tissues undergo many forms of disease that are frequently accompanied by inflammation. The somatosensory nerves innervating the inflamed area experience heightened excitability and generate and transmit pain signals. Even patients without cutaneous inflammation (diabetes with peripheral neuropathy) develop pain and often hyperesthesia. Hyperesthesia is defined as an increased sensitivity manifesting as a stimulus-dependent neuropathic pain. The most common hyperesthesia are allodynia and hyperalgesia. Allodynia is defined as pain after stimulation which is not normally painful (i.e. pain on light touch) and may be seen after different types of somatosensory stimuli are applied to many different tissues. Meanwhile hyperalgesia is defined as increased pain form a stimulus that normally provokes pain (i.e. out of proportion pain from a pin prick). Hyperpathia is a painful syndrome characterized by an abnormally painful reaction to a stimulus, especially a repetitive stimulus, as well as an increased threshold. Hyperpathia may occur with allodynia, hyperesthesia, hyperalgesia, or dysesthesia. Faulty identification and localization of the stimulus, delay, radiating sensation, and aftersensation may be present, and the pain is often explosive in character.

Hyperalgesia is induced by platelet-activating factor (PAF) which comes about in an inflammatory or an allergic response. This seems to occur via immune cells interacting with the peripheral nervous system and releasing pain-producing chemicals (cytokines and chemokines).

Long-term opioid (e.g. heroin, morphine) users and those on high-dose opioid medications for the treatment of chronic pain, may experience hyperalgesia and experience pain out of proportion to physical findings, which is a common cause for loss of efficacy of these pain medications over time. As it can be difficult to distinguish from tolerance, opioid-induced hyperalgesia is often compensated for by escalating the dose of opioid, potentially worsening the problem by further increasing sensitivity to pain. Chronic hyperstimulation of opioid receptors results in altered homeostasis of pain signaling pathways in the body with several mechanisms of action involved. One major pathway being through stimulation of the nociceptors and blocking these receptors may therefore be a means of preventing the development of hyperalgesia.

Stimulation of nociceptive fibers in a pattern consistent with that from inflammation switches on a form of amplification in the spinal cord, long term potentiation. This occurs where the pain fibres synapse to pain pathway, the periaqueductal grey. Amplification in the spinal cord may be another way of producing hyperalgesia.

The release of proinflammatory cytokines such as interleukin-1 by activated leukocytes triggered by lipopolysaccharides, endotoxins and other signals of infection also increases pain sensitivity as part of sickness behavior, the evolved response to illness.

In neuropathic pain, $TxA_2$ synthase and hematopoietic $PGD_2$ synthase were significantly increased in the microglia while administration of DPr2 antagonist attenuates allodynia (Kanda et al. *Glia.* (2013) doi: 10.1002/glia.22487). Platelets play a key role in the development of peripheral inflammation and core localize with macrophages in the inflamed tissue. $TxA_2$/TPr signaling promotes allodynia while deletion of TPr reduced allodynia (Pierre et al. *J Invest Dermatol.* (2017) doi: 10.1016/j.jid.2016.09.036). A TPr|DPr2 DRA will help to alleviate pain in conditions of extreme cutaneous sensitivity include diabetes, sickle cell disease, shingles, sarcoidosis, vasculitis, carcinoma/paraneoplastic, Guillian-Barre syndrome, monoclonal gammopathy, critical illness, infections including HIV, varicella-zoster virus, leprosy, drug-induced including isoniazid, statins, amiodarone and immunosuppressive agents; toxins including ethanol and heavy metals; mechanical including post-amputation pain/phantom limb pain, spinal cord injury, nerve trauma, failed back surgery syndrome and reticulopathies cause by nerve root compression, systemic diseases, multiple sclerosis, stroke and opioid induced hyperalgesia.

In accordance with the above objects and others, the present invention is directed in part to a method of treating or ameliorating pain in a subject in need of treatment thereof, comprising administering a therapeutically effective amount of a TPr|DPr2 DRA to the patient.

TPr|DPr2 Dual Receptor Antagonist for Prevention and Treatment of Obesity, Metabolic Syndrome and Diabetes Diabetes is characterized by unusually high levels of blood glucose (hypoglycemia) either due to lack of insulin production (Type I) or insulin resistance/nonresponsive to insulin (Type II). Hyperglycemia impairs the integrity and function of the blood-brain barrier through the initiations of TxA$_2$/TPr signaling by inhibiting nitric oxide production (Zhao et al. *Oncotarget*. (2017) doi: 10.18632/oncotarget.16273). Furthermore, PGD$_2$/DP2 signaling induces apoptosis of islet cells, which produces insulin in the pancreas, and insulin secretions normalize with a DPr2 antagonist (Skritic et al. *PloS One*. (2018) doi: 10.1371/journal.pone.0208998) Therefore, PGD$_2$/DP2 may be an underlying cause of type 1 diabetes due to islet cell depiction.

In accordance with the above objects and others, the present invention is directed in part to a method of preventing, treating or ameliorating type 1 diabetes in a subject in need of treatment thereof, comprising administering a therapeutically effective amount of a TPr|DPr2 DRA to the patient.

Metabolic Syndrome

Lipid mediators play a key role in promoting obesity and its effect on end-organs including development of hypertension, insulin resistance and diabetes. High fat diet and obesity increase expression of COX-2 and cytosolic phospholipase A$_2$.

Obesity is associated with elevated levels of TxA$_2$. Furthermore, obesity markedly increases vascular thromboxane receptor expression. Obesity augments prostanoid dependent vasoconstriction, thereby promoting development of vascular disease, hypertension and thrombosis (Traupe et al. *Journal of Hypertension*. (2002) doi: 10.1097/00004872-200211000-00024). High fat diet and obesity are also associated with marked increase in lipocalin PGD$_2$ synthase>hematopoietic PGD$_2$ synthase (Fujimori et al. Scientific Reports. (2019) doi: 10.1038/s41598-018-38453-y). Consequently, plasma levels of PGD$_2$ are markedly elevated in obese. High fat diet also induces significant increase in expression of DPr2 receptors thereby markedly augmenting PGD$_2$/DPr2 signaling. PGD$_2$/DPr2 signaling during high fat diet induces weight gain, insulin resistance, hyperglycemia and hyperlipidemia which were reduced in PGD$_2$ knockout mice. PGD$_2$/DPr2 signaling suppresses lipolysis and promotes survival of adipose cells (Wakai et al. *Biophys Res Commun*. (2017) doi: 10.1016/j.bbrc.2017.06.053).

The well-known phenomenon of aspirin resistance in the obese or the elderly has been attributed to increased expression of cytosolic phospholipase A$_2$ and COX-2 which leads to increased generation of TxA$_2$. Platelet function inhibition by aspirin may be a matter of degree, rather than being "all or none." Accordingly, underdosing, poor absorption of aspirin, or increased platelet turnover or activation may also be a factor in aspirin nonresponse. During states of high platelet turnover and aggregation, aspirin may not be sufficient to inhibit TxA$_2$ production and such patients would likely benefit from direct inhibition of TxA$_2$ action.

Therefore, a TPr|DPr2 DRA will reduce obesity and obesity related diseases including type 11 diabetes, hypertension, hyperlipidemia and obesity induced end organ damage to heart, kidneys and liver, especially in patients who are aspirin resistant.

TPr|DPr2 Dual Receptor Antagonist for Prevention and Treatment of Fibrosis

Fibrosis, also known as fibrotic scarring, is a pathological wound healing in which connective tissue replaces normal parenchymal tissue to the extent that it goes unchecked, leading to considerable tissue remodeling and the formation of permanent scar tissue. Fibrosis is often involved in the development of many disease conditions and vice versa in which PGD$_2$ and TxA$_2$ play a role (Table 2).

Pulmonary: TPr is expressed in lung fibroblasts and is upregulated in fibroblasts from patients with idiopathic pulmonary fibrosis (IPF), as well as lung fibroblasts from mice treated with bleomycin. Genetic deletion of TPr in mice or treatment with a TPr antagonist markedly attenuates bleomycin-induced lung fibrosis (Blackwell et al. *Grantome*. (2019) Project: 1R01HL151016-01). Furthermore, in IPF, mast cell products such as histamine and PGD$_2$ are increased in the lung tissue, contributing to the recruitment of eosinophils that damage the lung by release of oxygen free radicals (Libby. D. N.; The Eosinophil In Idiopathic Pulmonary Fibrosis. *CHEST*, 1987). To systematically characterize the molecular changes associated with silicosis and to discover potential therapeutic targets, a transcriptomics analysis of diseased human lung tissues acquired during transplantation was compared with lungs from silica-induced mouse model; and the effect of a TPr|DPr2 DRA, Ramatroban on the progression of silicosis was evaluated in the silica-induced mouse model (Pang et al. Theranostics. (2021) doi: 0.10.7.150/thno.47627). In this model Ramatroban alleviated silica-induced pulmonary inflammation by inhibiting NLRP3 inflammasome, IL-1beta and caspase-1, reducing infiltration with macrophages, lymphocytes and neutrophils; inhibiting fibrosis and resulting cardiopulmonary dysfunction while restoring lung compliance (FIG. 4). This provides proof for the effectiveness of dual DPr2 and TPr antagonism in reducing inflammation and fibrosis.

Post-COVID lung fibrosis and post-COVID interstitial lung disease (PC-ILD) are emerging as highly significant complications of COVID-19 pneumonia. The bronchoalveolar lavage fluid in COVID-19 pneumonia exhibits markedly increased levels of thromboxane B$_2$>PGD$_2$ (Archambault et al. MedRxiv. (2020) doi: 10.1101/2020.12.04.20242115) A causal link between TxA$_2$ and PGD$_2$ generation in the lungs with pulmonary fibrosis has been demonstrated in the mouse model of silicosis. Ramatroban, a dual TPr|DPr2 DRA, markedly inhibited infiltration by macrophages, neutrophils and lymphocytes; while significantly reducing lung fibrosis (Pang et al. *Theranostics*. (2021) doi: 10.7150/thno.47627). Therefore, TPr|DPr2 DRA are promising agents for prevention and treatment of Post-COVID lung fibrosis and interstitial lung disease.

Cardiac: PGD$_2$/DPr2 signaling has pro-apoptotic and pro-inflammatory effects and thereby plays a key role in fibrosis of lungs, liver, heart, kidneys and skin. As an example, PGD$_2$ induces apoptosis of cardiomyocytes via DPr2, thus increasing risk of myocardial injury and fibrosis. Administration of a DPr2 antagonist in anoxic mice, protects hearts from myocardial infarction and reduces infarct size (Zuo et al. *EMBO Mol Med*. (2018) doi: 10.15252/emmm.201708237). The document U.S. Pat. No. 9,693,998 B2 describes methods of treating, preventing, and/or ameliorating fibrosis syndrome, and in particular cardiac fibrosis, by administration of a selective TxA$_2$/TPr antagonist, including ramatroban as listed in the detailed description. However, the document fails to highlight the dual receptor antagonism of both the TxA$_2$/TPr and PGD$_2$/TPr receptors by ramatroban which would be more effective than TxA$_2$/TPr alone. Furthermore, selective TxA$_2$/TPr antagonism does not account for the TxA$_2$-11dhTxB$_2$-PGD$_2$/TPr2 cooperation.

Liver: Increased production of TxA$_y$, contributes to endothelial dysfunction and increased hepatic vascular tone. In carbon tetrachloride induce cirrhosis (liver fibrosis), TxA$_2$/TPr directly induces cirrhosis (liver scarring) by promoting collagen-I accumulation which was abrogated with TPr antagonism (Rosado et al. Hepatology. (2013) doi: 10.1002/hep.26520). IL-33 is significantly elevated in liver cirrhosis. IL-33 stimulates the production of $PGD_2$. $PGD_2$/DPr2 leads to release of IL-13, causing pathologic tissue remodeling and fibrosis (McHedlidze et al. *Immunity*. (2013) doi: 10.1016/j.immuni.2013.07.018)

Renal: The type 2 immune response directly induces fibrosis by increasing collagen expression in tubulointerstitial (renal) fibrosis which was reduced in DPr2 deficient mice (Ito et al. *J Am Soc Nephrol*. (2012) doi: 10.1681/ASN.2012020126). Furthermore, in a rat model of puromycin aminonucleoside nephrosis. $TxA_2$ production was enhanced along with massive proteinuria in which inhibition of the $TxA_2$ pathways significantly reduced proteinuria (Shibauta et al. *Kidney International*. (1991) doi: 10.1038/ki.1991.115).

Scleroderma and Progressive systemic sclerosis: $PGD_2$/DPr2 signaling promotes a type 2 allergic immune response leading to recruitment of eosinophils which causes many fibrotic conditions including inflammatory bowel disease, progressive systemic sclerosis or scleroderma, atopic dermatitis and pulmonary fibrosis.

Vascular modifications and complications significantly contribute to development of fibrosis by exacerbating inflammation, hypoxia, vascular remodeling, etc. $TxA_2$/TPr obstructs blood flow secondary to blood clotting and vasoconstriction leading to hypoxia and cell death/organ dysfunction particularly in the kidneys (Li et al. Oncotarget. (2018) doi: 10.18632/oncotarget.25005). Subsequently, growth factors are released to promote angiogenesis or blood vessel growth in which $TxA_2$/TPr signaling is a critical intermediary (Nie et al. *Biochem Biophys Res Commun*. (2000) doi: 10.1006/bbrc.1999.1840). Angiogenesis promotes vascular permeability (leakage) contributing to systemic sclerosis.

Peritoneal membrane dysfunction and peritoneal fibrosis/sclerosis: Peritoneal dialysis (PD) is a technique for substitution of kidney function. Due to the use of a biological membrane with bioincompatible dialysis solutions the peritoneum suffers alterations that limit its use and long-term viability. This bioincompatibility ultimately leads to ultrafiltration failure, irreversible structural fibrosis, and potentially, encapsulating peritoneal sclerosis (EPS). Clinical risk parameters and functional data of peritoneal membrane transport, such as high-fast small solute transport and lower free water transport, are conventionally used to predict functional and structural peritoneal membrane damage. Treatment for more than 4 years with bioincompatible PD solutions is known to present the highest risk for EPS. Episodes of peritonitis, glucose degradation products (GDPs), epithelial to mesenchymal transition (EMT) of mesothelial cells, and time are factors promoting peritoneal dysfunction and EPS. Podoplanin expression in the peritoneum is associated with fibrosis during encapsulating peritoneal sclerosis (Braun et al. *Nephrology Dialysis Transplantation*. (2011) doi:10.1093/ndt/gfq488) and podoplanin is a natural ligand for CLEC-2 receptors (FIG. 2) A TPr|DPr2 DRA inhibit-, the podoplanin-CLEC2-$TxA_2$/TPr signaling thereby reducing peritoneal fibrosis, encapsulating peritoneal sclerosis and ultrafiltration failure (FIG. 2).

TABLE 2

Role of thromboxane $A_2$/TPr and $PGD_2$/DPr2 signaling in fibrosis in various organs; and role of the dual receptor antagonist in prevention and/or treatment of fibrosis

| Organs | Type of injury | $PGD_2$ | Efficacy of anti-$PGD_2$/DPr2 | $TxA_2$ | Efficacy of anti-$TxA_2$/TPr | Disease conditions |
|---|---|---|---|---|---|---|
| Lung | Acute | ↑ | + | ↑ | + | Pneumonia (bacteria/viral), Goodpasture syndrome, Pulmonary vasculitis, ALI, ARDS |
| | Chronic fibrotic disease | ↑ | + | ↑ | + | COPD, pneumoconiosis, interstitial lung disease, idiopathic pulmonary fibrosis, chronic pulmonary embolism. |
| Liver | Acute | ↑ | + | ↑ | + | Hepatitis (viral, drug-induced, toxic), acute liver failure, ischemia/reperfusion injury |
| | Chronic fibrotic disease | ↑ | + | ↑ | + | alcoholic liver disease, hepatic steatosis, NASH, Drug-induced liver injury, end stage liver disease, cirrhosis |
| Heart | Acute | ↑ | + | ↑ | + | Acute Myocarditis, ischemia/reperfusion injury, anoxia, ischemic heart disease, myocardial infarction |
| | Chronic fibrotic disease | ↑ | + | ↑ | + | Cardiomyopathy, chronic hypoxia, Pulmonary hypertension, congenital heart disease |
| Kidney | Acute | ↑ | + | ↑ | + | Acute kidney injury Obstructive uropathy, Acute glomerulonephritis, renal vasculitis, |
| | Chronic fibrotic disease | ↑ | + | ↑ | + | Chronic kidney disease SLE/lupas nephritis, Diabetic nephropathy, Hypertensive nephroselerosis Chronic glomerulonephritis |
| Skin | Acute | ↑ | + | ↑ | + | Acute mechanical skin injury, frostbite, burns, |
| | Chronic fibrotic disease | ↑ | + | ↑ | + | Systemic Sclerosis (scleroderma), Atopic dermatitis, Psoriasis Dermatitis Pressure wounds, Eczema |

*The data includes experiments performed in vitro and in vivo.

Since $PGD_2$/DPr2 axis promotes cell death. $TxA_2$/TPr-11dh$TxB_2$-$PGD_2$/DPr2 interactions would initiate or exacerbate fibrosis and multiorgan failure in diseases with high $TxA_2$ levels even during blockade of one receptor as described above. In accordance with the above objects and others, the present invention is directed in part to a method of treating or ameliorating fibrotic disease in a subject in need of treatment thereof, comprising administering a therapeutically effective amount of a TPr|DPr2 DRA to the patient.

TPr|DPr2 Dual Receptor Antagonist for Prevention and Treatment of Bone Diseases Secondary to Osteoclast Deficiency Including Adynamic Bone Disease and Osteopetrosis Adynamic bone disease (ABD) is a common form of renal osteodystrophy among patients with chronic kidney disease. ABD has been reported in up to nearly 60% of all dialysis patients. ABD is characterized by low bone turnover, normal mineralization, and low to normal bone volume. Bone biopsies of patients with ABD show few osteoblasts and osteoclasts, decreased bone formation, and diminished activation frequency. ABD increases the risk of fractures and can promote soft tissue and vascular calcification with subsequent vascular events.

ABD results from parathyroidectomy or over suppression of PTH. Risk factors for ABD include peritoneal dialysis, glucocorticoid and bisphosphonate use, diabetes, menopause, hypogonadism, increasing age, malnutrition, systemic inflammation, calcimimetics, excessive vitamin D and/or calcium supplementation, high calcium dialysate, and calcium-based phosphate binders.

In renal bone disease, there is infiltration of bone tissue with bone marrow derived mast cells (Turner et al. *Journal of Bone and Mineral Research*. (2010) doi: 10.1002/jbmr.49). Mast cells produce $PGD_2$. Similar to cardiomyocytes, $PGD_2$/PDr2 signaling induces apoptosis of human osteoclasts which is prevented with a DPr2 antagonist (Yue et al. *Bone*. (2012) doi: 10.1016/j.bone.2012.06.003) Therefore, a TPr|DPr2 DRA will increase osteoclast number activity and overall activity thereby increasing bone turnover in ABD.

Osteopetrosis is a metabolic bone disease characterized by increased bone mass caused by polygenic disorders. Disorders in osteoclast formation and loss of osteoclast function are the main reasons for decreased bone resorption and increased bone mass. Recent studies have suggested that decreased bone resorption could be caused by abnormalities in the RANKL/RANK/OPG system, lack of c-Fos protein, and mutations in M-CSF, while mutations in the vacuolar (H*)-ATPase (V-ATPase) subunit, loss of CLC-7 chloride channels, and a shortage of cathepsin K are the most common reasons for osteopetrosis caused by bone resorption disorders. Bone marrow transplantation and the subsequent differentiation of hematopoietic stem cells from the implanted new bone marrow into mature and functioning osteoclasts is a treatment option for osteopetrosis. A TPr|DPr2 DRA by inhibiting osteoclast apoptosis, will promote survival of osteoclasts and reduce bone mass in osteopetrosis.

In accordance with the above objects and others, the present invention is directed in part to a method of treating or ameliorating bone disease in a subject in need of treatment thereof, comprising administering a therapeutically effective amount of a TPr DPr2 DRA to the patient.

TPr|DPr2 Dual Receptor Antagonist for Treatment of Muscular Dystrophy

Muscular Dystrophy (MD) is a group of 30+ diseases that causes progressive weakness and loss of muscle mass due to mutations in dystrophin, a protein needed to form healthy muscle. Duchenne MD (DMD) comprises half of MD. Becker MD (BMD) is the 2nd most common form of MD; 1 in 30,000 boys; BMD is milder and slowly progresses compared to DMD; symptoms may not be seen until teens, mid-20s or later. Limb-Girdle MD (LGMD) can affect as many as 1 in 14,500 and causes weakness and wasting of the muscles in the proximal arms and legs. Complications of muscular dystrophy include inability to walk, breathing problems, scoliosis, cardiomyopathy and swallowing problems. There is no effective cure. Treatment to-date is to manage symptoms or slow progression.

Delta-sarcoglycan (DSG) is a transmembrane glycoprotein which forms as a complex, the dystrophin-associated glycoprotein complex (DGC). The DGC plays a central role in maintaining integrity of the cell membrane by linking the extracellular matrix ("ECM"; a substance containing collagen, elastin, proteoglycans, glycosaminoglycans, and fluid, produced by cells and in which the cells are embedded) and cytoskeleton. Dystrophin works to connect sarcolemma to cytoplasmic actin cytoskeleton. Dysfunction produces membrane instability, elevated intracellular calcium levels and disrupted nitric oxide signaling. Absence of dystrophin in Duchenne muscular dystrophy (DMD) causes progressive breakdown of muscle cells. In the heart, loss of dystrophin leads to abnormally increased intracellular calcium, degradation of contractile proteins, fibrosis, and myocardial death.

Patients with DMD, BMD and LGMD develop cardiomyopathy. Cardiomyopathy is the primary cause of death amongst DMD patients. DMD patients develop an insidious decline in cardiac function leading to heart failure and can also develop arrhythmias, with the potential for sudden cardiac death, even with minimal decrease in cardiac function by physical symptoms or echocardiography.

The cellular damage characteristic of DMD is also associated with increased formation of reactive oxygen species, or oxidative stress. (Grosso, et al., Brain Dev. 2008; 30(6): 391-5.doi: 10.1016/j.braindev.2007.11.005). These free radicals can react with membrane phospholipids to form isoprostanes, which circulate freely after release by phospholipase, and the relatively stable 15-F2t-isoprostane (F2-IsoP) is a primary biomarker of in vivo oxidative stress. Plasma F2-IsoP levels are increased in DMD patients (Grosso, et al., cited above), and urinary F2-IsoP levels are increased in heart failure patients, where they correlate with the severity of the disease. In addition to heralding cellular stress, isoprostanes can also be the source of damage via activation of the thromboxane/prostanoid receptor (TPr), and $F_2$-IsoP signaling through the TPr causes vasoconstriction and ischemia reperfusion injury (FIG. 1).

$PGD_2$ induced inflammation plays a role in DMD, increasing with aging in DMD patients (Nakagawa et al. *Clinica Chimica Acta* (2013). doi: 10.1016/j.cca.2013.03.031). Expression of hematopoietic $PGD_2$ synthase was observed in the hyalinated necrotic muscle fiber in DMD and polymyositis and was associated with muscle necrosis (Okinaga et al. Acta *Neuropathologica* (2002) doi: 10.1007/s00401-002-0567-z). Due to the proapoptotic role of $PGD_2$/DPr2 signaling, skeletal muscle degeneration/fibrosis is likely mediated through $PGD_2$/DPr2 signaling which is not blocked by TPr antagonism alone.

Several TPr antagonists have been developed over the past 30 years (Dogne J-M, et al., Exp. Opin. Ther. Patents 11: 1663-1675 (2001). Certain TPr antagonists either with or without concomitant $TxA_2$ synthase inhibitory activity, including ifetroban (BMS), ridogrel (Janssen), terbogrel (B), UK-147535 (Pfizer). GR 32191 (Glaxo), S-18886 (Sender), vapiprost and BAY u 3405 or ramatroban (Bayer) have been proposed as treatments for muscular dystrophy. However, targeting-$TxA_2$/TPr-11dh$TxB_2$-$PGD_2$/DPr2 axis will have superior efficacy compared to a selective antagonist of TPr in the treatment of MD or its sequelae or complications.

In accordance with the above objects, the present invention provides for methods of treating muscular dystrophy by administering a therapeutically effective amount of a TPr|DPr2 DRA to target skeletal muscle degeneration/fibrosis and oxidative stress.

TPr|DPr2 Dual Receptor Antagonist for Prevention and Treatment of Infection

In one embodiment, the present invention describes using a TPr|DPr2 DRA antagonist as an immunomodulator for modulating an immune response to a microbe when $PGD_2$ is a causative factor in stunting the patient's immune response. The method comprises administering to a patient in need thereof an effective amount of a TPr|DPr2 DRA. The present invention also describes methods for treating microbial infections said methods comprising administering to a patient in need thereof an effective amount of a TPr|DPr2 DRA. In preferred embodiments the patient is elderly and/or immune compromised. As used herein the term "immune comprised" means having a weakened immune system, which reduces the body's ability to fight infections and other diseases.

Certain embodiments include treatment with TPr|DPr2 DRA of infections in patients are who are immune compromised due to aging, organ transplantation, use of immunosuppressive drugs, autoimmune diseases etc. and related sequelae and complications.

Virus entry of respiratory infections into the body is blocked by the host innate immune response, which is suppressed by naso-oral $PGD_2$/DPr2 signaling (Werder al. *Sci Tranl Med*. (2018) doi: 10.1126/scitranslmed.aao0052) Suppression of innate immune response by $PGD_2$/DPr2 signaling allows for viremia, viral entry into the brain (neurotropic coronaviruses), and vasculature leading to cardiovascular complications and multiorgan failure described below.

Platelet activation is a common complication of infections leading to risk of stroke, heart attacks and is a major cause of death during infection. The mechanism of platelet activation is the activation of platelet CLEC2 signaling by infections including HIV, dengue virus and *salmonella* (Hitchcock et al. *J Clin Invest*. (2015) doi: 10.1172/JCI79070), which is dependent on $TxA_2$ signaling.

The inventors propose that any of the therapeutic agents already invented and developed, yet to be invented, yet to be developed, or yet to be tested in clinical trials, as long as such agent is a TPr|DPr2 DRA, can be advantageously used to enhance the immune response to infections including viral, bacterial, fungal, parasitic, amoebic and neurotropic. Therefore the inventor proposes that antagonist of $TxA_2$/TPr or $PGD_2$/$DP_2$; or a TPr|DPr2 DRA such as ramatroban can be advantageously and safely used to treat any microbial infection that stimulates the production of $PGD_2$, and this forms the broad inventive concept comprising one embodiment of this patent application.

Certain embodiments include treatment of a patient with TPr|DPr2 DRA such as ramatroban. The use of TPr|DPr2 DRA such as ramatroban for this purpose can be extrapolated to all infections, acute and chronic, including RESPIRATORY INFECTIONS such as bronchiectasis, sinusitis, pneumonia, lung abscess, bronchopneumonia etc. caused by *mycoplasma*, influenza virus, respiratory syncytial virus, corona viruses including SARS-CoV2, bacterial and mycotic infections including tuberculosis etc.; GENITOURINARY INFECTIONS including urinary tract infections, pyelonephritis, and pyonephrosis; vaginal and uterine infections, GASTROINTESTINAL INFECTIONS such as *Clostridium difficile*, rota viruses, enteropathogenic *E. Coli, salmonella, shigella* SARS-CoV-2; HEPATIC INFECTIONS including hepatitis, liver abscess, etc., SKIN and BONE infections including osteomyelitis, skin ulcers including venous, arterial, neuropathic, pressure ulcers, Buruli ulcer, and calciphylaxis: CNS infection including meningitis, tuberculosis, brain abscess, as well as other infections including HIV/AIDS, leprosy etc.

In a specific embodiment, viral infections include but are not limited to SARS-CoV, SARS-CoV-2, MERS, HIV. AIDS, hepatitis types A, B and/or C, dengue virus, influenza, West Nile virus, ebola, congenital Zika syndrome. Bowenoid papulosis, California encephalitis, shingles, Chikungunya. Chronic active Epstein Barr virus infection, congenital rubella, eastern equine encephalitis, hantavirus pulmonary syndrome, herpes simplex encephalitis, herpes zoster ophthalmicus, herpes zoster oticus, human t-cell leukemia virus types 1, 2 and/or 3, Japanese encephalitis, Kaposi sarcoma, Kyasanur Forest disease, La Crosse encephalitis, Jamestown Canyon Virus, Snowshoe Hare Virus, St Louis Encephalitis, Marburg hemorrhagic fever, measles, molaret meningitis, monkeypox, multicentric castleman disease, neonatal herpes, nipah virus encephalitis, omsk hemorrhagic fever, parainfluenza virus type 3, poliomyelitis, progressive multifocal leukoencephalopathy, rabies, rubella, unicentral castleman disease, western equine encephalitis, human papillkina virus, yellow fever, Zika virus infection and/or small pox, chicken pox.

In another specific embodiment, bacterial infections include but are not limited anthrax, atypical mycobasteriosis, familial, balantidiasis, brucellosis, bubonic plague, buruli ulcer, cat scratch disease, chanroid, cholera, *Clostridium sordellii* infection, cutaneous anthrax, disseminated infection with *Mycobacterium avium* complex, *Flavimonas oryzihabitans* infection, glanders, granuloma inguinale, group B strep disease in newborns, *Haemophilus influenzae*, hansen's disease, human granulocytic chrlichiosis, *klebsiella* infection, legionnairs' disease, lemierre sudnrome, *listeria* infection, lyme disease, melioidosis, mycetoma, *Mycobacterium abscessus, Mycobacterium avium* complex infections, *mycobacterium* chelonae. *mycobacterium* fortuitum, *mycobacterium* gordonac, *mycobacterium kansasii, mycobacterium* malmoense, *mycobacterium marinum, mycobacterium* xenopi, necrotizing fasciitis, nontuberculous mycobacterial lung disease. *Pasteurella multocida* infection, pinta, pyomyositis, Q fever, rheumatic fever, rocky mountain spotted fecer, sennetse fever, shigellosis, Staphylococcal food poisoning, *Stenotrophomonas maltophilia* infection, Streptococcal group A or group B invasive disease, tetanus, tropic sprue, tularemic, typhus, waterhouse-friderishcens syndrome, whipple disease, whopping cough and/or yaws.

In a specific embodiment, parasitic infections include but are not limited to malaria and leishmaniasis. In another specific embodiment, amoebic infections include are but not limit to negleria *fowleri.*

In a preferred embodiment, the infection is a neurotropic infection cause by a neurotropic coronavirus or prion disease.

All patients with infection or bacteremia are at risk of developing sepsis and represent early phases in the continuum of sepsis severity. Sepsis exists on a continuum of severity ranging from infection and bacteremia to sepsis and septic shock, which can lead to multiple organ dysfunction syndrome (MODS) and death. Infection and bacteremia may be early forms of infection that can progress to sepsis.

Septic shock: Septic shock is a type of vasodilatory or distributive shock. Septic shock is defined as sepsis that has circulatory, cellular, and metabolic abnormalities that are associated with a greater risk of mortality than sepsis alone. Clinically, this includes patients who fulfill the criteria for sepsis that, despite adequate fluid resuscitation, require vasopressors to maintain a mean arterial pressure (MAP)≥65 mmHg and have a lactate>2 mmol/L (>18 mg/dL).

Multiple organ dysfunction syndrome: Multiple organ dysfunction syndrome (MODS) refers to progressive organ dysfunction in an acutely ill patient, such that homeostasis cannot be maintained without intervention. It is at the severe end of the severity of illness spectrum of both infectious (sepsis, septic shock) and noninfectious conditions (e.g., systemic inflammatory response syndrome or SIRS from pancreatitis).

MODS can be classified as primary or secondary: PRIMARY MODS is the result of a well-defined insult in which organ dysfunction occurs early and can be directly attributable to the insult itself (e.g., renal failure due to rhabdomyolysis). SECONDARY MODS is organ failure that is not a direct response to the insult itself but is a consequence of the host's response (e.g., acute respiratory distress syndrome in patients with pancreatitis).

Systemic inflammatory response syndrome (SIRS): SIRS is considered a clinical syndrome that is a form of dysregulated inflammation. It was previously defined as two or more abnormalities in temperature, heart rate, respiration, or white blood cell count. SIRS may occur in several conditions related, or not, to infection. Noninfectious conditions classically associated with SIRS include autoimmune disorders, pancreatitis, vasculitis, thromboembolism, burns, or surgery.

Blockers of TPr and/or $PGD_2$/DPr2 receptor can be used for treating and/or preventing the worsening of sepsis, septic shock, toxic shock syndrome, multiple organ failure (MODS), or systemic inflammatory response syndrome (SIRS).

In another embodiment, the present invention describes methods for treating or preventing the worsening of conditions including but not limited to sepsis, septic shock. MODS and/or SIRS as defined above. The method comprises administering to a patient in need thereof an effective amount of a TPr|DPr2 DRA such as ramatroban.

Certain embodiments include treatment of a patient with ramatroban. The use of antagonist of a TPr|DPr2 DRA such as ramatroban for this purpose can be extrapolated to all conditions related to infections with microbes including viruses, bacteria, and fungi, sepsis, septic shock, endotoxemia, toxic shock syndrome, MODS, and/or SIRS as defined above.

TPr|DPr2 Dual Receptor Antagonist for Prevention and Treatment Respiratory Disease Acute lung injury (ALI) and acute respiratory distress syndrome (ARDS), characterized by overwhelming lung inflammation, are associated with high mortality. Cigarette smoke is a major cause of ALI/ARDS. A DPr2 antagonist was shown to decrease proinflammatory immune cells and proinflammatory cytokine levels in the bronchoalveolar lavage fluid and reduce lung histopathological alterations in mice exposed to cigarette smoke (Hussain et al. Life Sci. (2019) doi: 10.1016/j.lfs.2018.11.039). Therefore. $PGD_2$ may play a role in respiratory disease and infections. TPr antagonists have also proven useful to treat respiratory diseases such as emphysema (Horiguchi et al. *Arzneimittelforschung*. (2002) doi: 10.1055/s-0031-1299963). The antipathogenic, anti-inflammatory, antiapoptotic and antiplatelet effects of a TPr|DPr2 DRA make TPr|DPr2 DRA's such as ramatroban promising treatments for respiratory diseases including but not limited to acute lung injury, hospital-acquired pneumonia, acute respiratory distress syndrome, cystic fibrosis, acute asthma, emphysema, chronic pulmonary emphysema, chronic obstructive pulmonary disease, chronic bronchitis and/or smoking/smoking inducing lung injury, community-acquired pneumonia and/or primary or secondary pulmonary hypertension.

$TxA_2$ and $PGD_2$ are significantly increased and play a role in pulmonary arterial hypertension, a life-threatening disease characterized by high blood pressure in the lungs. Blocking the $PGD_2$/DPr2 pathway attenuates pulmonary hypertension by reducing the type 2 inflammatory response. Further efficacy will be demonstrated upon blockade of both $TxA_2$/TPr and $PGD_2$/DPr2 with a TPr|DPr2 DRA (Chen et al. JEM. (2018) doi: 10.1084/jem.20171767; Christman et al. *NEJM*. (1992) doi: 10.1056NEJM199207093270202).

Community Acquired Pneumonia

Community acquired pneumonia, especially in the elderly, is a major cause of morbidity and mortality, especially in the winter months. $PGD_2$ signaling plays a critical role in the inability of the elderly to mount an adequate host immune response to the pathogens. (Zhao et al. J Clin Invest. (2011) doi: 10.1172/JCI59777) The airways of the elderly generate more $PGD_2$ which has a suppressive effect on the following components of host immune response. First, type III interferons, the innate host immune response critical in limiting viral replication, progression, and transmission are downregulated by $PGD_2$/DPr2 axis. Second. $PGD_2$/DPr2 axis suppresses the cell mediated immune response to pathogen via the ILC2-Interleukin 13-MDSC pathway.

Similar to COVID-19 infection, many infections such as influenza are associated with microvascular thrombosis and therefore, a TPr|DPr2 DRA has an advantage over selective TPr or selective DPr2 antagonists.

Compositions and Methods of Treatment (Combinations) of TPR|DPr2 Dra Antagonists with Other Agents for Prevention and Treatment of Diseases and Conditions As used herein, "drug," "pharmaceutical agent," "pharmacologically active agent," "pharmaceutically acceptable." or any other similar term means any therapeutic, chemical or biological material or compound depending on the disease in question and on the condition of the patient by the methods previously known in the art and/or by the methods taught in the present invention that induces a sustained or immediate biological or pharmacological effect. The effect can be local, such as providing for a local effect, or it can be systemic. An embodiment of the present invention relates to a dosage form device and the mode of making dosage forms of a TPr|DPr2 DRA with any pharmaceutically acceptable drug that is suitable for delivery by the present invention so as to achieve a dual delivery effect either by (i) immediate release of both drugs or (ii) initial immediate delivery followed by a slow sustained delivery or (iii) slow sustained delivery of both drugs. Included are broad classes of compounds normally delivered into the body orally, parenterally, and/or through body surfaces and membranes, including skin. Such drug combinations are listed below.

TPr|DPr2 DRA Antagonists in Combination with Other Anti Cancer Therapies

Checkpoint inhibitor therapies, which 'unblock' an existing immune response or which unblock the initiation of an immune response are very effective at treating cancer in a subgroup of subjects. However, the subgroup of subjects is relatively small, constituting only approximately 25% of the cancer subject population (i.e., the "responding subject population"). Accordingly, while checkpoint inhibitors are extremely effective at treating cancers in the responding subject population, approximately 75% of cancer subjects will not respond to the therapy. In addition, even in the responding population the response is not always complete or optimal. Since many of the immune checkpoints are regulated by interactions between specific receptor and ligand pairs, monoclonal antibodies or other agents can be used to block this interaction and prevent immunosuppression. The two checkpoint receptors that have received the most attention in recent years are CTLA-4 and PD-1.

A specific strategy for the treatment of cancer is to combine a checkpoint inhibitor with a TPr|DPr2 DRA. The combination of a TPr|DPr2 DRA and a checkpoint inhibitor enhances or prolongs the anti-tumor response, and/or enable a subject to respond to a checkpoint inhibitor, and/or enable the reduction of the toxicity or the dose of a checkpoint inhibitor in a subject.

Another strategy for the treatment of cancer is to combine a TPr|DPr2 DRA with a therapeutic. Chemotherapy has been proven to be effective in the treatment of cancer. Further, the administration of a TPr|DPr2 DRA may enhance or prolong the effects of the biologic therapeutic and/or chemotherapy.

In a specific embodiment of other cancer therapies, for example, the anti-proliferative agent is a microtubule stabilizing agent such as paclitaxel, or a derivative, analogue, such as docetaxel (Taxotere®), or mixture thereof; a platinum-based chemotherapeutic compound such as cisplatin, carboplatin, iproplatin, and related compounds; or other conventional cytotoxic compounds.

In a second aspect, the invention features a method of preventing, decreasing, reducing, or inhibiting tumor growth in a subject in need thereof, comprising administering to the subject a TPr|DPr2 DRA in combination with any other cancer therapy, wherein tumor growth is decreased, reduced, or inhibited.

In a third aspect, the invention features a method of reducing the amount of a chemotherapeutic agent necessary to achieve a desired therapeutic effect, comprising administering the chemotherapeutic agent with a TPr|DPr2 DRA. More specifically, the TPr|DPr2 DRA is ramatroban and the chemotherapeutic agent is an anti-proliferative agent, such as paclitaxel, or a derivative, analogue, or a mixture thereof; a platinum-based chemotherapeutic compound such as cisplatin, carboplatin, iproplatin, and related compounds; or other conventional cytotoxic compounds. In one embodiment, the amount of chemotherapeutic agent necessary to achieve a desired therapeutic effect, such as, for example, inhibition of tumor growth, is at least 20% less in the presence of co-administered a TPr|DPr2 DRA. In a more specific embodiment, the amount of chemotherapeutic agent necessary is about 40-50% less in the presence of a TPr|DPr2 DRA.

In a fourth aspect, in one embodiment, the present invention provides a method of treating cancer or initiating, enhancing, or prolonging an anti-tumor response in a subject in need thereof comprising administering to the subject a TPr|DPr2 DRA in combination with an agent that is a checkpoint inhibitor. In one aspect, the checkpoint inhibitor is a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein which may be CTLA-4, PDL1, PDL2, PD1, B7-13. B7-14, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein which may be CTLA-4, PDL1, PDL2, PD1, B7-H3, B7-H4, BTLA, HVEM. TIM3, GAL9. LAG3, VISTA, KIR, 2B4, CD160, CGEN-15049. CHK 1, CHK2, A2aR, B-7 family ligands or a combination thereof. More specifically, the TPr|DPr2 DRA is ramatroban, and the checkpoint inhibitor is an oral checkpoint inhibitor, CCX559.

TPr|DPr2 DRA Antagonists in Combination with Other Anti-Diabetic Therapies

Obesity increases the risk for the development of cardiovascular disease and is often complicated by the development of Type 11 diabetes, heart disease and chronic kidney disease (CKD). Strategy for the treatment of diabetes is the administration with a TPr|DPr2 DRA in combination with a metformin; SGLT2 inhibitors including but not limited to canagliflozin, dapagliflozin and empagliflozin; dipeptidyl peptidase-4 inhibitors including but not limited to sitagliptin, vildagliptin, saxafliptin and linagliptin; incretin mimetic (GLP-1 receptor agonists) including but not limited to exenatide, liraglutide, albiglutide or dulaglutide; alpha-glucosidase inhibitors including but not limited to acarbose and miglitol or a combination thereof.

TPr|DPr2 DRA Antagonists in Combination with Other Modulators of Lipid Mediators In addition to $PGD_2$ other lipid mediators play a role in maladaptive immune responses. Cysteine leukotrienes (cysLT), particularly leukotrienes $D_4$ and $E_4$, initiate a weak type 2 immune response from T helper 2 (Th2) cell. However, when combined with $PGD_2$, cysLT caused a greater additive enhancement on Th2 cell activation and type 2 immune responses (Xue et al. *J Immunol.* (2012) doi: 10.4049/jimmunol.1102474. $PGD_2$/DPr2 inhibition with the addition of inhibiting cysLT pathway would further abolish the often-harmful type 2 immune responses observed in many inflammatory disease conditions.

Strategy of combining a TPr|DPr2 DRA in combination with cysLT inhibitors is beneficially applied for the treatment of type 2 immune responses in disease conditions that include but are not limited to eosinophilic esophagitis, asthma, allergic rhinitis, mast cell activation syndrome, chronic rhinosinusitis, acute promyelocytic leukemia, Churg-Strauss syndrome, drug allergies, chronic eosinophilic leukemia, eosinophilic peritonitis, graft eosinophilia in transplant organs and graft rejection, graft versus host disease, idiopathic hypereosinophilic syndrome, lymphatic filariases, Crohn's disease, mastocytosis, urticaria pigmentosa, anaphylaxis and immune suppressive diseases. In a specific embodiment, the cysLT inhibitor is a cysLT receptor inhibitor including but not limited to Monteleukast, Zafirlukast, or Pranlukast. In further embodiments, the cysLT inhibitor is a cysLT synthesis inhibitor such as Zileuton.

Other Combinations

Strategy for the treatment of Duchenne Muscular Dystrophy is the administration of TPr|DPr2 DRA in combination with corticosteroids. In a specific embodiment, the corticosteroid is Deflazacort.

Strategy for the treatment of sickle cell disease is the administration of TPr|DPr2 DRA in combination with pharmaceutically acceptable treatment for sickle cell disease including but not limited to hydroxyurea. L-glutamine and voxelotor.

Strategy for the treatment of type 2 inflammatory such as in asthma is the administration of TPr|DPr2 DRA in combination with bronchodilators and antihistamines.

Strategy for the treatment of cardiovascular disease including Buerge's syndrome is the administration of TPr|DPr2 DRA in combination with vasodilators including pentoxifiline or iloprost.

Strategy for the treatment of hair loss is the administration of TPr|DPr2 DRA in combination with minoxidil.

Strategy for the treatment of viral infections is the administration of TPr|DPr2 DRA in combination with antiviral agents including, but not limit to remdesivir, oseltamivir, zanamivir, peramivir and baloxavir marboxil.

Strategy for the treatment of Parkinson's disease is the administration of TPr|DPr2 DRA in combination with dopaminergic drugs including but not limit to L-dopa (levodopa), ropinirole, pramipexole and rotigotine.

Strategy for the treatment of an inflammatory, allergic or autoimmune disorder is the administration of a TPr|DPr2 DRA used in combination with other immunosuppressive agents which include but are not limited to glucocorticoids including prednisone, prednisolone and dexamethasone.

Strategy for the treatment of Alzheimer's disease is the administration of TPr|DPr2 DRA in combination with anticholinergic drugs including but not limit to atroprine, *belladonna* alkaloids, benztropine mesylate, clidinium, cyclopentolate, darifenacin, dicyclomine, fesoterodine, flavoxate, glycopyrrolate, homatropine hydrobromide, hyoscyamine, ipratrpium, orphenadrine, oxybutynin, propantheline, scopolamine, methscopolamine, colifenacin, tiotropium, tolterodine, trihexyphenidyl and trospium.

Strategy for the treatment of neurological disorders including Alzheimer's disease and Parkinson's disease by co-administration or combination of a TPr|DPr2 DRA with sodium oligomannate (GV-971).

In a specific embodiment in the above combination therapies, whether formulated as a combination or coadministered separately the TPr|DPr2 DRA is ramatroban, a pharmaceutically acceptable salt of ramatroban or a derivative of ramatroban.

Pharmaceutical Compositions, Dosage and Administration

A TPr|DPr2 dual receptor antagonist of the present invention may be administered by any pharmaceutically effective route. Thus, a TPr|DPr2 DRA of the invention may be formulated in a pharmaceutically acceptable manner such that the resulting formulation may be administered orally, intranasally, rectally, vaginally, sublingually, buccally, parenterally, aurally, ocularly or transdermally, as dictated by the properties of the formulation and the indication.

In certain embodiments, a DRA of the invention may be formulated in a pharmaceutically acceptable oral dosage form. In specific embodiments, oral dosage forms may include, but are not limited to, oral solid dosage forms and oral liquid dosage forms. In further embodiments, oral solid dosage forms include, but are not limited to, tablets, capsules, caplets, powders, pellets, multiparticulates, beads, spheres and any combinations thereof. These oral solid dosage forms may be formulated as immediate release, controlled release, sustained (extended) release or modified release formulations. An oral solid dosage form of the present invention may also contain pharmaceutically acceptable excipients such as fillers, diluents, lubricants, surfactants, glidants, binders, dispersing agents, suspending agents, disintegrants, osmogens, tableting aids, chemical-enhancers (cell-envelope disordering compounds and solvents or binary systems containing cell-envelope disordering compounds and solvents), water-soluble polymers, water-swellable polymers (osmopolymer or hydrogel), copolymers (plasticizers and tackifiers), homopolymers, matrix material, pH modifiers, pigments, antioxidants, viscosity-increasing agents, film-forming agents, granulation aid, flavoring agents (flavorants), erodible polymeric matrix, sweetener, coating agents, solubilizing agents, and combinations thereof. In another embodiment, depending on the desired release profile, the oral solid dosage forms of the present invention may contain a suitable amount of controlled-release agents, extended-release agents, or modified-release agents.

In specific embodiments, a DRA is delivered to a subject using matrix controlled-release devices, osmotic controlled-release devices, multiparticulate controlled-release devices, solvent-activated release devices, diffusion-controlled release devices, stimulus-responsive releases devices, chemically-activated release devices, pulse-release devices, extended-release devices, delayed-release devices, sustained release devices (including ophthalmic drug delivery systems), erosion-controlled release devices, implantable drug delivery devices, modified-release drug devices, intraoral slow-release devices, enteric coated controlled-release devices. Such delivery devices may be fabricated in various geometries including bilayer, wherein the core comprises a drug layer and a sweller layer adjacent to each other; trilayer, wherein the core comprises a sweller layer "sandwiched" between two drug layers; and concentric, wherein the core comprises a central sweller composition surrounded by the drug layer. In a preferred embodiment, both drug layers may contain a TPr|DPr2 DRA or one layer may contain a TPr|DPr2 DRA while the other may contain a pharmacologically active agent.

In certain embodiments of the present invention, the TPr|DPr2 DRA may be formulated into a dosage form suitable for parenteral use. For example, the dosage form may be lyophilized powder, a solution, suspension (e.g., depot suspension).

In other embodiments, the TPr|DPr2 DRA may be formulated into a topical dosage form such as, but not limited to, a patch, a tape, a sheet, a dressing, a gel, a paste, a cream, an ointment, an emulsion, a liniment, a balm, a lotion, and any other form known to those skilled in the art.

In another embodiment, a TPr|DPr2 DRA is administered via ocular topical delivery including topic ocular eye-drops, viscous solutions, suspensions, emulsions, ointments, aqueous gels and polymeric inserts. In a specific embodiment, a TPr|DPr2 DRA is administered through intraocular injection.

In an embodiment, a TPr|DPr2 DRA is administered via the peritoneal dialysis (PD) solution to a patient with end-stage renal disease. In a specific aspect the TPr|DPr2 DRA is added to the peritoneal dialysis solution at the point of use. In another embodiment the TPr|DPr2 DRA comes premixed into the PD solution.

The amount of the composition that will be effective in the treatment of a particular disorder or condition will depend on the nature of the disorder of condition, which can be determined by standard clinical techniques. In addition, in vitro or in vivo assays may optionally be employed to help identify optimal dosage ranges. The precise dose to be employed in the formulation will also depend on the route of administration, and the seriousness or advancement of the disease or condition and should be decided according to the practitioner and each patient's circumstances. Effective doses may be extrapolated from dose-response curved derived from in vitro or animal model test systems. For example, an effective amount of the composition can readily be determined by administering graded doses of the composition and observing the desired effect.

The method of treatment according to this invention comprises administering internally or topically to a patient in need thereof a therapeutically effective amount of the composition comprised of a TPr|DPr2 DRA. The purity of the mixture includes, but is not limited to 0.01% to 100%, depending on the methodology used to obtain the compound (s). In a preferred embodiment, doses of a TPr|DPr2 DRA and pharmaceutical compositions containing the same are an efficacious, nontoxic quantity generally selected from the range of 0.01 to 200 mg/kg of body weight depending on age of the patient and the indication for which the drug is prescribed. Persons skilled in the art using routine clinical testing are able to determine optimum doses for the particular ailment being treated. The following examples are provided for illustrative purposes only and are not intended to limit the scope of the invention.

In addition to the conventional oral and intravenous routes, depending on the organ system involvement, the severity of the clinical condition, the age group to be treated this invention may be practiced by delivery of a TPr|DPr2 DRA via different routes of administration as described below and appropriate doses to be delivered in the therapeutically affective manner depending on the route of administration to target a particular organ system or the body as a whole. This is illustrated by the following examples.

In a patient with respiratory infection. TPr|DPr2 DRA is formulated as an aerosol (inhaler, nebulizer). In a patient with impaired gastrointestinal absorption secondary to a state of shock, gastrointestinal infection, gangrene, mnalabsorption, noncompliance for example amongst children, states of unconsciousness. TPr|DPr2 DRA is formulated for parenteral including transdermal, subcutaneous, intramuscular, intravenous, or intranasal or oral route including sublingual, trans-buccal, for example, a spray into the mouth. In children with sickle cell disease or with noncompliance, TPr|DPr2 DRA is formulated as a flavored or non-flavored effervescent tablet or chewable tablets including gummies. In majority of cases. TPr|DPr2 DRA is advantageously administered by oral delivery either as a tablet or capsule without any limitations. The oral formulation can be of immediate release or slow release formulation, manufactured using standard techniques inherent in the art.

The therapeutic dose of TPr|DPr2 DRA needed depends on disease condition and the route of administration. This is illustrated by the following examples. In a patient with upper respiratory tract infection, a small dose of TPr|DPr2 DRA ranging from 1 mg to 150 mg administered one to four times a day by the different routes of oral or parenteral administration. In a patient with septic shock. TPr|DPr2 DRA is administered intravenously at a high dose ranging from 1 mg/kg to 100 mg/kg depending on the body weight of the patient. Over a period of 24 hours, TPr|DPr2 DRA can be formulated as a bolus injection or as a slow continuous infusion. For intravenous delivery. TPr|DPr2 DRA can be formulated either as a plastic or glass capsule, ampule, vial, prefilled syringe, or as a premixed bag with TPr|DPr2 DRA added to a vehicle such as dextrose, saline, ringer lactate, sodium bicarbonate, or any other suitable vehicle. When local delivery of TPr|DPr2 DRA is needed in the eye, the drug is advantageously administered as eyedrops. In a chronic kidney disease patient undergoing peritoneal dialysis, TPr|DPr2 DRA is administered via the peritoneal dialysis (PD) solution, either premixed into the PD solution or added at the point of use.

The inventor proposes that any of the therapeutic agents already invented and developed, yet to be invented, yet to be developed, or yet to be tested in clinical trials, as long as such agent is a TPr|DPr2 DRA, can be advantageously used for chemoprophylaxis and treatment of various diseases that are the subject of this inventive concept.

EXAMPLES

Example 1. Pneumonia and Lung Injury in the Elderly with Community Acquired Pneumonia Community acquired pneumonia, especially in the elderly, is a major cause of morbidity and mortality, especially in the winter months. PGD2 signaling plays a critical role in the inability of the elderly to mount an adequate host immune response to the pathogens. (Zhao et al. *J Clin Invest*. (2011) doi: 10.1172/JCI59777) The airways of the elderly generate more PGD2 which has a suppressive effect on the following components of host immune response.
1. The innate host immune response mediated by interferon pathway is critical to limit viral replication, progression, and transmission. Interferon pathways are downregulated by PGD2/DPr2 axis.
2. PGD2/DPr2 axis suppresses the cell mediated immune response to pathogen via the ILC2-Interleukin 13-MDSC pathway (FIG. 1).

Similar to COVID-19 infection, many infections such as influenza lead to endothelial injury, platelet activation, platelet-neutrophil partnership, thromboinflammation and microvascular thrombosis. A TPr|DPr2 DRA acts as an antiplatelet-antithrombotic agent in addition to its immunomodulatory effects.

An 85-year old resident of a nursing home develops a serious upper respiratory infection with high fever, cough, and shortness of breath requiring admission to the hospital. Serology is positive for influenza. Patient is treated with Ramatroban with rapid recovery. A 80 year old resident of the same nursing home with influenza infection is not treated with Ramatroban, developed respiratory distress, is transferred to the intensive care unit with systemic inflammatory response syndrome, and expires.

Example 1b. COVID-19 and Acute Respiratory Distress Syndrome (ARDS

A novel coronavirus, SARS-CoV-2, was identified in late 2019 as the causative agent "coronavirus disease 2019" (COVID-19). Direct viral infection of the endothelial cell and diffuse endothelial inflammation occurs systemically traversing multiple organs and sets into motion the cycle of endothelial injury, platelet activation, platelet-neutrophil partnership, release of NET's, thromboinflammation and microvascular thrombosis. Many patients develop anti-phospholipid antibodies that further lead to thrombosis. Elevated levels of D-dimer have been observed in COVID-19 and other prothrombotic disorders, and correlate with illness severity.

Example 1c. Disseminated Intravascular Coagulopathy (DIC)

Diffuse hypercoagulable state and diffuse endothelial activation or panendothelitis, with microvascular thrombi that contain fibrin as well as platelets are common pathogenetic mechanisms in disseminated intravascular coagulation (DIC). Platelet activation and endothelial cell-platelet interaction play a central role in all forms of DIC. DIC may present as an acute, life-threatening emergency or a chronic, subclinical process, depending on the degree and tempo of the process and the contribution of morbidities from the underlying cause. Common causes of DIC include the following: Sepsis from a variety of organisms (bacterial, fungal, viral, and parasitic); Malignancy, especially acute promyelocytic leukemia, mucinous tumors (e.g., pancreatic, gastric, ovarian), and brain tumors; Trauma, especially to the central nervous system; Obstetrical complications, including preeclampsia, retained dead fetus, acute fatty liver of pregnancy; Intravascular hemolysis, often due to acute hemolytic transfusion reaction (AHTR) in the setting of ABO incompatible transfusion, but also in other forms of hemolysis such as in severe malaria. Other causes include heat stroke; crush injuries; amphetamine overdose; fat embolism; vascular abnormalities, including aortic aneurysm and Kaposiform hemangioendothelioma; rattlesnake or other viper bite (considered by some to be another type of coagulopathy and/or thrombotic microangiopathy other than DIC); hereditary protein C deficiency; acute solid organ transplant rejection; antiphospholipid antibody syndrome (APS).

Example 1d: Pneumonia and ARDS Complicated by Pulmonary Fibrosis

A 70-year-old Japanese male is admitted to hospital with COVID-19 and ARDS requiring mechanical ventilation. In addition to conventional supportive therapy, patient is treated with ramatroban 75 mg twice a day leading to rapid recovery. Patient is discharged home after 5 days. Since the patient has allergy rhinitis, he is given a prescription for ramatroban to continue as an outpatient. After 2 months, patient is back to his normal self and his chest X-ray reveals complete resolution of the infiltrates with no evidence of any pulmonary fibrosis or scarring. Pulmonary function tests arm normal as is the diffusion capacity for carbon monoxide (DLCO). It is noted that several such patients who did not receive ramatroban after recovery from acute COVID-19 illness have developed chronic lung disease with patchy pulmonary fibrosis, chronic mild hypoxia, and impaired DLCO. A retrospective analysis of data on COVID-19 patients reveals that patients treated with ramatroban have shorter recovery time, rapid improvement in lymphocyte counts, rapid recovery from thrombocytopenia, less need for mechanical ventilation, and when ramatroban is continued for week to months after discharge from the hospital, there is reduced fibrosis and scarring in the lungs with better lung function.

Example 2: Kawasaki Disease and MIS-C in Children

Example 2a. MIS-C: A family living in Kobe, Japan has 2 fraternal twins, both boys (B1 and B2), aged 6 years old. Both boys develop COVID-19 disease with high fever and URTI. The boy, B1, has allergic rhinitis and asthma and has been receiving ramatroban (Baynas®) for the past 2 months. Both boys recover over a period of 1 week. B1 continues to take ramatroban during and following recovery. Ten days after recovery. B2 develops fever, chest pain, vomiting, diarrhea and rash. B2 has severe lymphopenia, urinary thromboxane B2 levels are 5× upper limit of normal (ULN); D-dimers are 100×ULN; troponin is 10×ULN and BNP is 100×ULN. Following admission to the hospital B2 continues to deteriorate and develops toxic shock syndrome requiring pressor support. B2 is prescribed ramatroban followed by clinical recovery over a 4 day period accompanied by marked improved in laboratory parameters. The sibling. B1, remains healthy while continuing to take ramatroban for his allergic rhinitis and asthma with ramatroban serving as prophylaxis against Kawasaki like disease.

Example 2b: Kawasaki Disease

Kawasaki Disease (KD) is an acute febrile illness of unknown etiology that primarily affects children younger than 5 years of age. KD is thought to be caused by an aberrant immune reaction to infection in genetically predisposed patients. Clinical signs include fever, rash, swelling of the hands and feet, irritation and redness of the whites of the eyes, swollen lymph glands in the neck, and irritation and inflammation of the mouth, lips, and throat. KD is a leading cause of acquired heart disease in children. Serious complications include coronary artery dilatations and aneurysms. It is controversial whether the standard treatment, intravenous immunoglobulin and aspirin, substantially decreases the development of these coronary artery abnormalities or not.

During the acute and subacute phases of KS, platelet count and tendency for platelet aggregation increase with marked elevation in plasma level of thromboxane B2 ($TxB_2$), a thromboxane A2 metabolite, and reduction in 6-keto-prostaglandin F1α (PGF1α), a prostacyclin metabolite, during the acute phase. Long term follow up demonstrates partial suppression of $TxB_2$ with therapy but almost undetectable $PGF_{1\alpha}$ levels. In addition, markers of endothelial stimulation or damage such as von Willebrand factor, thrombin-antithrombin III, tissue factor, and soluble thrombomodulin are increased. Further, the presence of a large aneurysm induces stagnation of blood flow, facilitating spontaneous intravascular coagulation. Histopathological examination of coronary artery aneurysms in KD demonstrates eosinophilic infiltration in the periadventicial tissue, a $PGD_2$/DPr2 response. This support use of TPr|DPr2 DRA to address both $TxA_2$ and $PGD_2$ mediated pathology.

Example: Two 17-month old twins are suffering from persistent fever, vomiting, diarrhea, and slight cough. Fever continues during early hospitalization, and each of the children develops bilateral bulbar conjunctival congestion without exudatem, labial and lungual erythema. Kawasaki disease is diagnosed. One child is treated with a TPr|DPr2 DRA, in conjunction with steroids and intravenous immunoglobulin. The other child is treated only with steroids and intravenous immunoglobulin. The child treated with TPr|DPr2 DRA recovers uneventfully within 48 hours of admission and is discharged. The child treated conventionally continues to have high grade fever and develops coronary artery aneurysms.

Example 3. Septic Shock

In patients with septic shock as a consequence of gangrenous bowel, Ramatroban is administered intravenously at a dose of 150 mg BID along with standard of care treatment including antibiotics leading to rapid recovery without development of SIRS or DIC.

Example 4. Viral Infection in Animal Facility

In a large animal shelter facility, there was an outbreak of viral infection largely affecting dogs and cats leading to deaths of many older animals, while the young animals survived. Blood testing showed that $PGD_2$ and $TxB_2$ were elevated in the aged animals compared to the young or middle-aged animals. After starting ramatroban, the was a marked decline in the infection severity in the older animals along with a marked decrease in mortality.

Example 5. Metabolic Disease a) In a prospective clinical trial, patients with obesity are randomized to receive ramatroban versus placebo for a period of a year. Ramatroban promotes weight loss and reduces serum hemoglobin A1c, lipid and glucose levels. Furthermore, patients on ramatroban exhibit lower blood pressure, require lower doses of anti-hypertensives and have less microalbuminuria.
b) In a cross-sectional epidemiological study, compared to the control group, the patients taking ramatroban have lower prevalence of obesity, a lower BMI, and decreased serum levels of HbA1c and lipids.
c) In a prospective randomized control trial, obese subjects are prescribed low fat diet for a period of 6 months (stage 1) followed by ad libitum diet for the next 6 months (stage 2). All subjects are randomized to receive ramatroban versus placebo for the total study duration of 12 months. Subjects on ramatroban have significantly more loss of fat mass and weight compared to control subjects at the end of stage 1. During stage 2, patients on ramatroban have significantly less tendency to regain the weight that had been lost during stage 1. It is also found that at the end of both stages that subjects in the ramatroban group exhibit lower levels of blood lipids and glucose.
d) In a prospective clinical trial, patients with cardiovascular disease that are
e) aspirin group versus the ramatroban group.

Example 6: Neurological Diseases

Patient 6a, an 82 year old man with a four year history of Parkinson's disease, has a two year history of progressive imbalance with frequent falls. He has a one year history of progressive memory loss, particularly in remembering names and faces, with rare visual hallucinations. After treatment with ramatroban, Patient reports a subjective improvement in his sense of balance in the first week of treatment, and stops falling thereafter. In addition, he no longer experiences hallucinations. There was significant improvement in cognitive function at 4 months.

Patient 6b, a 72-year-old woman with a two-year history of Parkinson's disease, has a six month history of rapid physical decline and becomes wheelchair dependent. She also develops progressive dementia with frequent formed visual hallucinations and social withdrawal. Two months after ramatroban is started, Patient experiences significant improvement in physical functioning, reduction in hallucinations, and marked improvements in cognitive ability and sociability.

Example 7: Chilblains

A 60 year old man develops chilblains every winter with swelling of the hand associated with bluish discoloration and occasional ulceration. He informs the inventors that the same symptoms have reoccurred every winter for the past 15 years. The patient is treated with TPr|DPr2 DRA, leading to complete resolution of chilblains for the rest of the winter season.

Example 8: TAO a) A 40-year-old man, chronic smoker, presents with gangrene involving the two toes of his right foot. Upon further investigation, he is diagnosed to have TAO. The patient is treated with Ramatroban, which leads to partial resolution and healing of the gangrenous toes following improvement in the blood flow to the lower extremities.
b) In a randomized control trial of 30 patients with TAO, 15 are randomized to Ramatroban along with standard of care versus 15 to the standard of care group. The patients in the Ramatroban group demonstrate improvement in blood flow and resolution of ischemic lesions compared to the control group.

Example 9: Sickle Cell Disease

In a prospective clinical trial, patients with steady state SCD or vaso-occlusive crisis (VOC) are randomized to ramatroban 50-75 mg BID versus placebo. Ramatroban reduces markers of inflammation, leucocyte activation and platelet activation while reducing the onset of VOC in patients with steady state SCD. Furthermore in SCD patients with VOC, ramatroban decreases D-dimer and plasma myeloperoxidase levels while reducing onset of acute chest syndrome compared to placebo.

Example 10: Kidney Disease

Rhabdomyolysis is caused by skeletal muscle injury and the subsequent release of breakdown products from damaged muscle cells into systemic circulation. Heme released from necrotic muscles activate platelets leading to the formation of macrophage extracellular traps that play a role in the development of acute kidney injury. Heme induced platelet activation is mediated by CLEC2 (FIG. 2). Consistent with the above, platelets activated by CLEC2 interact with neutrophils and macrophages which subsequently release extracellular traps (Sung et al. Nature. (2019) doi: 10.1038/s41467-019-10360-4). Formation of extracellular traps plays a major role in kidney injury (Okubo et al. Nature Medicine. (2018) doi: 10.1038/nm.4462) and is likely mediated by CLEC2 because podoplanin, the natural ligand for CLEC2, is expressed on podocytes in the kidney. The involvement of podoplanin-CLEC2 signaling indicates TPr as a target in AKI and other kidney discuses including collapsing focal segmental glomerulosclerosis, chronic kidney disease (CKD), cardiorenal syndrome, hepatorenal syndrome, allergic interstitial nephritis, progression of CKD and progression of AKI to CKD.

Patients with chronic kidney disease or heart failure are randomized to receive ramatroban versus placebo prior to cardiac catheterization. There is significantly less dye nephrotoxicity and acute kidney injury in patients treated with ramatroban compared to placebo Example 11: Cardiorenal Syndrome The following description exemplifies the inventors' clinical observations and inventive method of treatment if a patient were to exhibit Patients hospitalized for acute heart failure are randomized to receive ramatroban versus placebo. There is significantly less development of cardiorenal syndrome and acute kidney injury with shorter hospitalization in patients treated with ramatroban compared to placebo Example 12: Dysfunction of the Arteriovenous Shunt Created for Hemodialysis Vascular Access Furthermore, urinary excretion of lipocalin type $PGD_2$ synthase (L-PGDS) is a common biomarker of many kidney diseases, indicating a role for $PGD_2$. In unilateral ureteral obstruction, markers of fibrosis, collagen I and plasminogen activator inhibitor-1, are suppressed in DPr2 deficient mice (Ito et al. *JASN*. (2012) doi: 10.1681/asn.2012020126) Therefore, $PGD_2$/DPr2 plays a role in kidney fibrosis and subsequent organ failure.

Hemodialysis patients are dialyzed using either an arteriovenous (AV) fistula or a graft. i.e., a surgically made connection between an artery and a vein that allows the high arterial pressure to dilate and arterialize the wall of the vein. Fistula or graft failure and eventual occlusion occur most commonly as a result of the progressive narrowing of the venous anastomosis; for native fistulas, failure occurs most commonly as a result of the narrowing of the outflow vein. The primary underlying pathophysiologic mechanism responsible for causing the failure is intimal hyperplasia at the anastomotic site. Stenoses along the venous outflow and in intragraft locations (for prosthetic PTFE grafts) are also common and require appropriate treatment.

Podoplanin is the natural ligand for the platelet CLEC2 receptor. In a murine deep venous thrombosis (DVT) model of inferior vena cava stenosis, podoplanin was significantly expressed in the vessel wall of mice with a thrombus (blood clot) compared to those without (Payne et al. *Blood*. (2017) doi: 10.1182/blood-2016-09-742999). Therefore, podoplanin expression on the venous limb of AV fistula or graft leads to platelet activation and causes thrombosis thereby leading to AV fistula or graft failure.

The following description exemplifies the inventors' clinical observations and inventive method of treatment if a patient were to exhibit Patients with end-stage kidney disease are randomized to receive ramatroban versus placebo prior to creation of arteriovenous fistula for hemodialysis for a period of 6 months. Follow up over the next 5 years demonstrates that in patients treated with ramatroban compared to placebo there is significantly decreased incidence of venous stenosis, number of vascular access procedures needed to restore patency and failure of the fistula.

Example 13: Buerger's Disease or Thromboangiitis Obliterans

Male smokers 20-50 years of age with TAO are randomized to receive ramatroban versus aspirin for a period of 12 months. All patients can be prescribed standard therapies including pentoxifylline, iloprost, calcium antagonists, statins and low molecular weight heparin or oral anticoagulants. In the rematroban group there is significantly less development of ulcers in the fingertips and toes, acrocyanosis, necrosis and loss of substance. There is increase in blood flow in the *dorsalis* pedis and posterior tibial pulses arteries by doppler examination with a decrease in need for surgical procedures and amputations. Improvement was seen of active vascular lesions and pain symptoms.

Example 14: Chemoprophylaxis Against Post-Pneumonia Pulmonary Fibrosis and Interstitial Lung Disease Patients with acute viral pneumonia including COVID-19 are randomized to receive ramatroban versus placebo in addition to conventional therapy. It is observed that in the ramatroban group there is significantly more rapid resolution of pneumonia during the hospitalization, and significantly reduced lung fibrosis coupled with higher lung compliance upon long term follow up Example 15. Pneumoconiosis with Pulmonary Fibrosis and Interstitial Lung Disease Non-smoking stone crushers are randomized to receive ramatroban versus placebo and are followed for a period of 5 years. Stone crushers receiving chemoprophylaxis with ramatroban exhibit significantly reduced lung fibrosis coupled with higher lung compliance.

Example 16. Primary Pulmonary Hypertension

A 35-year-old women presents with shortness of breath and palpitations for one year, complaining of compressive chest pain on exertion, but no cough, wheeze, sputum, hemoptysis or leg swelling. Patient is diagnosed to have primary pulmonary hypertension. There is no response to conventional therapy with sildenafil or bosentan. Addition of ramatroban leads to significant clinical improvement.

Example 17. Alzheimer's Disease (AD)

AD patients are randomized to four treatment groups that receive ramatroban, sodium oligomannate (GV-971), ramatroban+sodium oligomannate and placebo. The long-term follow-up of these patients reveal improvement of cognition and memory in the first 3 treatment groups compared with placebo, with the best efficacy observed in the combination of ramatroban with sodium oligomannate.

Example 18. Chemoprophylaxis with Ramatroban to Support Vaccination for Microbial Infection A 30-year old African patient with sickle cell disease (SCD) has a past history of multiple vaso-occlusive crisis (VOC), acute chest syndrome (ACS) and ischemic cerebrovascular accidents. Patient is administered the AstraZeneca vaccine as prophylaxis against COVID-19. The day prior to the vaccine, the patient is started on ramatroban 75 mg twice a day orally which is continued for a period of one month. The same regimen is repeated at the time of the second dose of the vaccine. The patient has a robust antibody response and there is no recrudescence or recurrence of VOC, ACS, myocardial infarction or stroke. Other similar patients with SCD are found to experience high incidence of thrombotic events after COVID-19 vaccines.

Example 19. Anti-Allergic, Anti-Inflammatory Combination

A 40-year-old male has suffered from severe asthma and allergic rhinitis since the age of 10 years, resistant to all conventional therapies including steroids. Addition of ramatroban to his conventional therapeutic regimen leads to a 25% improvement in symptoms. In order to further optimize the management a combination tablet containing ramatroban 75 mg and montelukast 5 mg is administered twice a day. Because of noncompliance, the patient is switched to a combination tablet containing 150 mg slow release ramatroban and 10 mg Montelukast. This leads to an additional 50% improvement in symptoms.

Example 20. Combination of Ramatroban with Immune Checkpoint Therapy

A 56-year-old non-smoker male is hospitalized for acute abdominal pain, melena and vomiting. Distended abdomen and decrease bowel sounds were observed during the physical examination. Initial laboratory results revealed disseminated intravascular coagulation and high levels of tumor marker carcinoembryonic antigen. Colonic biopsy demonstrates well-differentiated adenocarcinoma. Patient is treated with oral immune checkpoint inhibitor CCX559 but without response. To sensitize the tumor microenvironment to immune checkpoint therapy patient is switched to a combination tablet of ramatroban and CCX559, twice daily leading to enhanced response.

We claim:

1. A method of prevention or treatment of a disease, dysfunction or condition in a mammal characterized by thromboxane $A_2$ stimulated signaling by thromboxane prostanoid (TP) receptor and by $PGD_2$ stimulated signaling by D Prostanoid 2 (DP2) receptor which comprises administering to the mammal in need thereof an effective amount of a pharmaceutical composition comprising a dual receptor antagonist of both receptors DP2 and TP.

2. The method as claimed in claim 1 wherein said dual receptor antagonist of DP2 for prostaglandin $D_2$ and TP for thromboxane $A_2$ comprises ramatroban, a pharmaceutically acceptable salt or a derivative thereof.

3. A method of treating a disease or condition characterized by or associated with stimulation of both DP2 and TP signaling, which comprises administering to a patient in need thereof an effective amount of ramatroban, a pharmaceutically acceptable salt or a derivative thereof wherein the disease or condition is a viral infection caused by SARS-CoV-2.

4. The method as claimed in claim 1 wherein said disease, dysfunction or condition is selected from (a) an infectious illness caused by or associated with a prion, virus, bacteria, fungus, protozoa, parasite or helminth, viral infections corona viruses, rotavirus, a neurotropic virus, dengue virus, or HIV; (b) a hemolytic disease; (c) snake bite; (d) a kidney disease; (e) a cardiovascular disease; (f) a metabolic disease; (g) thromboembolic disease; (h) a neurological disease or condition; (i) pain; (j) amyloidosis; (k) fibrotic disease; (l) muscular dystrophy; (m) bone disease; (n) diabetes mellitus; (o) a disease caused by hyperactive type 2 immune response; (p) autoimmune disease; (q) cancer; (r) vasculitis; (s) degenerative disease; (t) allergic disorder; (u) smoking, smoking-induced lung injury; (v) pneumoconiosis; (w) traumatic disorder; (x) inflammatory condition or disease; (y) hereditary disease; (z) neuropsychiatric condition or disease; (aa) pain; (bb) obstetric complication and (cc) premature birth.

5. The method of claim 1 wherein said composition is administered in a dosage of 1 mg to 500 mg per day depending on route of administration, severity of illness and body weight.

6. The method as claimed in claim 1 wherein the disease, dysfunction or condition results from a viral infection wherein the virus is selected from 229E (alpha coronavirus), NL63 (alpha coronavirus), OC43 (beta coronavirus), HKU1 (beta coronavirus), MERS-CoV, SARS-CoV, SARS-CoV-2, HIV, AIDS, hepatitis types A, B and/or C, dengue virus, influenza, West Nile virus, ebola, congenital Zika syndrome, Bowenoid papulosis, California encephalitis, shingles, Chikungunya, Chronic active Epstein Barr virus infection, congenital rubella, eastern equine encephalitis, hantavirus pulmonary syndrome, herpes simplex encephalitis, herpes zoster ophthalmicus, herpes zoster oticus, human t-cell leukemia virus types 1, 2 and/or 3, Japanese encephalitis, Kaposi sarcoma, Kyasanur Forest disease, La Crosse encephalitis, Jamestown Canyon Virus, Snowshoe Hare Virus, St Louis Encephalitis, Marburg hemorrhagic fever, measles, molaret meningitis, monkeypox, multicentric castleman disease, neonatal herpes, nipah virus encephalitis, omsk hemorrhagic fever, parainfluenza virus type 3, poliomyelitis, progressive multifocal leukoencephalopathy, rabies, rubella, unicentral Castleman disease, western equine encephalitis, human papilloma virus, yellow fever, Zika virus infection, small pox, and/or chicken pox.

7. The method as claimed in claim 1 wherein said pharmaceutical composition comprises or is administered in conjunction with a vaccine selected influenza vaccine, HIV vaccine, hepatitis A, B or C vaccine, SARS-CoV-2 vaccine, pneumococcal vaccine, meningococcal vaccine, malaria vaccine, tetanus-diphtheria-pertussis vaccine, and zoster vaccine.

8. The method as claimed in claim 1 further comprising detecting a level of one or more biological molecules in the patient and determining a treatment regimen based on an increase or decrease in the level of one or more biological molecules, wherein the biological molecule is selected from the group consisting of lipopolysaccharide (LPS), LPs-binding protein (LBP), 16S rDNA, sCD14, intestinal fatty acid binding protein (I-FABP), zonulin-1, Collagen 1a1 and 3a1, TGF-β, fibronectin-1, hs-CRP, IL-1β, IL-6, IL-33, fibrinogen, MCP-1, MIP-1α and -1β, RANTES, sCD163, TGF-β, TNF-α, a biomarker of hepatocyte apoptosis, and a combination thereof.

9. The method as claimed in claim 8 wherein the one or more biological molecules is obtained from blood, skin, hair follicles, saliva, oral mucous, vaginal minucous, sweat, tears, epithelial tissues, urine, semen, seminal fluid, seminal plasma, prostatic fluid, pre-ejaculatory fluid (Cowper's fluid), excreta, biopsy, ascites, cerebrospinal fluid, lymph, brain, tissue extract sample or biopsy sample.

10. A pharmaceutical composition for treatment of a disease or condition characterized by or associated with stimulation of both DP2 and TP receptor signaling, said composition comprising an effective amount of a dual receptor antagonist of DP for prostaglandin $D_2$ and TP for thromboxane $A_2$ and a pharmaceutically acceptable carrier.

11. The composition as claimed in claim 10 wherein said dual receptor antagonist of DP2 for prostaglandin $D_2$ and TP for thromboxane $A_2$ comprises ramatroban, a pharmaceutically acceptable salt or a derivative thereof.

12. The composition as claimed in claim 10 further comprising including one or more drugs selected from the group of immunomodulators immunosuppressants cysteine leukotriene antagonists inhibitor anti-asthmatic bronchodilators; vasodilators; nitrates; phosphodiesterase-5 inhibitors antidiabetic agents; SGLT2 inhibitors; dipeptidyl peptidase-4 inhibitors; incretin mimetic (GLP-1 receptor agonists); alpha-glucosidase inhibitors anti-sickling agent and/or sphinosine-1-phosphate modulator drugs.

13. The method as claimed in claim 4 wherein said disease, dysfunction or condition is selected from sepsis, septic shock, viremia, bacterial infections, bacteremia, fungemia, MODS and SIRS.

14. The method as claimed in claim 4 wherein said disease or condition is selected from an infectious illness caused by or associated with a respiratory syncytial virus or SARS-CoV-2.

15. The method as claimed in claim 4 wherein the disease, dysfunction or condition is acute lung injury, post-viral chronical hyperreactivity syndrome, hospital-acquired pneumonia, acute respiratory distress syndrome, cystic fibrosis, acute asthma, emphysema, chronic pulmonary emphysema, chronic obstructive pulmonary disease, chronic bronchitis and/or smoking/smoking inducing lung injury, community-acquired pneumonia and/or primary pulmonary hypertension; a respiratory disease, community acquired pneumonia, viral pneumonitis, viral gastroenteritis, viral myocarditis, viral encephalitis, viral hepatitis, alpha thalassemia, beta thalassemia, sickle cell disease, paroxysmal nocturnal hemoglobinuria autoimmune hemolytic anemia, hemolytic uremia syndrome and microangiopathic hemolytic anemia, lupus nephritis, diabetic nephropathy, renal flares, reduced glomerular filtration rate, chronic kidney disease (CKD), tubulointerstitial fibrosis, chronic kidney disease (CKD) of undetermined cause (CKDu), focal segmental glomerular sclerosis (FSGS), collapsing FSGS, acute kidney injury (AKI), polycystic kidney disease (PKD), hepatorenal syndrome or cardiorenal syndrome.

16. The method as claimed in claim 4 wherein the disease, dysfunction or condition is rhabdomyolysis-induced acute kidney injury, AKI, dye-induced nephrotoxicity, progression of AKI to CKD, lupus nephritis, allergic interstitial nephritis, transplant rejection, cardiorenal syndrome, collapsing FSGS, essential hypertension, hypertensive arterial sclerosis, malignant hypertension, pulmonary arterial hypertension, coronary artery aneurysms with or without Kawasaki disease, arterial aneurysms, aortic aneurysms, transthyretin amyloidosis, gangrene, calciphylaxis, calcific uremia arteriolopathy, frostbite, ischemia reperfusion injury of the heart, Takotsubo syndrome, cardiomyopathy, myocarditis, Takayasu arteritis, Moyamoya disease, vascular disease, Kawasaki disease, Moyamoya disease, Takotsubo syndrome, amyloid cardiomyopathy, arteriosclerosis and venous stenosis following creation of an AV fistula for hemodialysis, stroke, silent cerebral infarcts, multi-infarct dementia, restenosis after coronary angioplasty, restenosis after coronary stent implantation, coronary stent thrombosis, saphenous vein graft failure, peripheral vascular disease, Buerger's disease, stenosis of the AV fistula during hemodialysis, obesity, insulin resistance, aspirin resistance and type 2 diabetes, aspirin resistance, Aspirin-Exacerbated Respiratory Disease (AERD) or contraindication to aspirin use as in children, thrombotic microangiopathy (TMA), thrombotic thrombocytopenia purpura (TTP), hemolytic uremic syndrome (HUS), disseminated intravascular coagulation (DIC), microangiopathic hemolytic anemia (MAHA), pulmonary embolism (PE), deep venous thrombosis (DVT), venous thromboembolism (VTE), and arterial thrombosis, Alzheimer's disease, Parkinson's disease, dementia with Lewy bodies, Gaucher's disease, Huntington's disease, transmissible spongiform encephalopathies or prion diseases, depression, sleep and behavior disorders, cerebral malaria, age related neurodegeneration, virus, bacteria, fungus and amoeba induced encephalitis, vascular dementia, thrombotic thrombocytopenia purpura induced encephalopathy, post-sepsis syndrome, long-haul COVID and brain fog, multisystem inflammatory disease in children, amyotrophic lateral sclerosis, multi-infarct dementia, limbic-predominant age related TDP-43 encephalopathy (LATE), Zika induced microcephaly, amyloidosis, dialysis dementia, or chronic and acute neuroinflammation.

17. The composition as claimed in claim 12 wherein:
(a) the immunomodulator is selected from checkpoint inhibitors that target and/or interact with a ligand of CTLA-4, PDL1, PDL2, PD-1, B7-H3, B7-H4, BTLA, HVEM, TIM3, GALS, LAG3, VISTA, KIR, 2B4, CD160, CGEN-15049, CHK 1, CHK2, A2aR, B-7 family ligands or a combination thereof;
(b) the corticosteroid is selected from deflazacort, prednisone, prednisolone and dexamethasone;
(c) the immune suppressive agent is selected from tacrolimus, cyclosporine, mycophenolate mofetil, azathioprine and rapamycin;
(d) the cysteine leukotriene antagonist is selected from Montelukast, Zafirlukast, and Pranlukast;
(e) the leukotriene synthesis inhibitor is Zileuton;
(f) the anti-asthmatic bronchodilator is selected from beta2 adrenergic agonists and anticholinergic agent;
(g) the vasodilator is selected from iloprost; minoxidil; nitrates; and phosphodiesterase-5 inhibitors selected from sildenafil, vardenafil, tadalafil and avanafil;
(h) the antidiabetic agent is metformin;
(i) the SGLT2 inhibitor is selected from canagliflozin, dapagliflozin and empagliflozin;
(j) the dipeptidyl peptidase-4 inhibitor is selected from sitagliptin, vildagliptin, saxafliptin and linagliptin;
(k) the incretin mimetic (GLP-1 receptor agonists) is selected from exenatide, liraglutide, albiglutide and dulaglutide;
(l) the alpha-glucosidase inhibitor is selected from acarbose and miglitol;
(m) the anti-sickling agent is selected from hydroxyurea, L-glutamine oral powder, voxelotor and niprisan and/or sodium oligomannate (GV-971); and
(n) the sphinosine-l-phosphate modulator drug is selected from etrasimod, fingolimod, ozanimod, siponimod, ponesimod and amiselimod.

18. The method as claimed in claim 1 wherein
a) the dual receptor antagonist of DP2 and TP receptors is an antiplatelet and/or antithrombotic agent to prevent and/or treat a vascular or thrombotic disease or condition selected from thrombotic microangiopathy (TMA), thrombotic thrombocytopenia purpura (TTP), hemolytic-uremic syndrome (HUS), disseminated intravascular coagulation (DIC), microangiopathic hemolytic anemia (MAHA), pulmonary embolism (PE), deep venous thrombosis (DVT), venous thromboembolism (VTE), malignant hypertension, primary and secondary pulmonary arterial hypertension, coronary artery aneurysms with or without Kawasaki disease, arterial aneurysm, aortic aneurysms; gangrene, calciphylaxis, calcific uremia arteriolopathy, frostbite, Takotsubo syndrome, cardiomyopathy, Takayasu arteritis, Moyamoya disease, silent cerebral infarcts, multi-infarct dementia, restenosis after coronary angioplasty, restenosis after coronary stent implantation, coronary stent thrombosis, saphenous vein graft failure; peripheral vascular disease, Buerger's disease (Thromboangiitis obliterans), Kawasaki disease, venous stenosis following creation of an AV fistula for hemodialysis, hemolytic disease, alpha thalassemia, beta thalassemia, sickle cell disease, paroxysmal nocturnal hemoglobinuria, and microangiopathic hemolytic anemia (MAHA), venomous snake bite; neurological disease, Alzheimer's disease, Parkinson's disease, dementia with Lewy bodies, Gaucher's disease, Huntington's disease, transmissible spongiform encephalopathies or prion diseases, depression, sleep and behavior disorders, cerebral malaria, age related neurodegeneration, vascular dementia, thrombotic thrombocytopenia purpura, post sepsis syndrome, long COVID, brain fog, multisystem inflammatory disease in children, obstetrical complications, preeclampsia, retained dead fetus, acute fatty liver of pregnancy, intravascular hemolysis, acute hemolytic transfusion reaction (AHTR) in the setting of ABO incompatible transfusion, hemolysis as in severe malaria or crush injuries, amphetamine overdose, vascular abnormalities, aortic aneurysm and Kaposiform hemangioendothelioma, hereditary protein C deficiency, acute solid organ transplant rejection, antiphospholipid antibody syndrome (APS), pernio (chilblains or perniosis); cannabis arteritis and/or tobacco related thromboangiitis obliterans;

b) the dual receptor antagonist of DP2 and TP receptors is an immunomodulatory agent to prevent and/or treat hyperactive type 2 immune response, eosinophilic esophagitis, mast cell activation syndrome, chronic rhinosinusitis, acute promyelocytic leukemia, drug allergies, allergic interstitial nephritis, allergic interstitial cardiomyopathy or acute interstitial myocarditis, chronic eosinophilic leukemia, eosinophilic peritonitis, graft eosinophilia in transplant organs and graft rejection, graft versus host disease, idiopathic hypereosinophilic syndrome, lymphatic filariases, Crohn's disease, mastocytosis, urticaria pigmentosa and anaphylaxis; autoimmune diseases, rheumatoid arthritis, systemic lupus erythematosus, progressive systemic sclerosis, scleroderma, IgA vasculitis, Takayasu arteritis, giant cell arteritis, polyarteritis nodosa, ANCA-associated vasculitis, microscopic polyangiitis, granulomatosis with polyangiitis, allergic granulomatosis with polyangiitis (Churg-Strauss), immune complex small-vessel vasculitis, anti-glomerular basement membrane disease, cryoglobulinemic vasculitis, IgA vasculitis, hypocomplementemic urticarial vasculitis (anti-C1q vasculitis), Bahcet syndrome, Coggan's syndrome, single-organ vasculitis, primary central nervous system vasculitis, vasculitis associated with systemic disease and vasculitis associated with probable etiology, myasthenia gravis, celiac disease, Sjogren's syndrome, polymyalgia rheumatica, autoimmune encephalitis, alopecia areata, primary systemic vasculitis, small, medium and large vessel vasculitis, Castleman's diseases, juvenile idiopathic arthritis, psoriasis, polymyositis, relapsing polychondritis, adult-onset Still's disease, remitting seronegative symmetrical synovitis with pitting edema, uveitis, spondyloarthritides, periodic fever, familial mediterranean fever and aphthous stomatitis; vasculitis disease in systemic lupus erythematosus and/or a condition in which the innate immune response to the viral infection is blunted by failure of interferon lambda expression in response to the virus, allowing replication and propagation of the virus;

c) the dual receptor antagonist of DP2 and TP receptors is an antithrombotic, immunomodulatory and anti-inflammatory agent to prevent and/or treat kidney disease, acute kidney injury (AKI), rhabdomyolysis induced acute kidney injury, lupus nephritis, diabetic nephropathy, chronic kidney disease (CKD), tubulointerstitial fibrosis, IgA nephropathy, focal segmental glomerular sclerosis (FSGS), collapsing FSGS, polycystic kidney disease (PKD), hepatorenal syndrome, cardiorenal syndrome, renal involvement in allergic granulomatosis with polyangiitis, renal involvement in scleroderma, delayed allograft function, acute or chronic transplant rejection, and/or cardiorenal syndrome;

d) the dual receptor antagonist of DP2 and TP receptors is an antithrombotic, immunomodulatory and anti-inflammatory agent to prevent and/or treat neurological disease, Alzheimer's disease, Parkinson's disease, dementia with Lewy bodies, Gaucher's disease, Huntington's disease, transmissible spongiform encephalopathies or prion diseases, depression, sleep and behavior disorders, cerebral malaria, age related neurodegeneration, virus, bacteria, fungus, parasite and amoeba induced encephalitis, vascular dementia, thrombotic thrombocytopenia purpura induced confusion, post sepsis syndrome, long-haul COVID, brain fog, multisystem inflammatory disease in children, amyotrophic lateral sclerosis, multi-infarct dementia, limbic-predominant age related TDP-43 encephalopathy (LATE), Zika induced microcephaly, amyloidosis, dialysis dementia, and/or chronic and acute neuroinflammation;

e) the dual receptor antagonist of DP2 and TP receptors is an antithrombotic, immunomodulatory and anti-inflammatory agent to prevent and/or treat amyloid associated disease, Amyloid A amyloidosis, transthyretin amyloidosis leading to cardiomyopathy (Transthyretin Amyloid Cardiomyopathy (ATTR-CM)), hereditary amyloidosis, and/or wild-type amyloidosis or localized amyloidosis affecting the heart, lungs, liver, skin, kidneys, and/or brain;

f) the dual receptor antagonist of DP2 and TP receptors is an antifibrotic agent to prevent and/or treat a fibrosis-associated disease involving a lung, idiopathic pulmonary fibrosis, radiation-induced fibrosis, pneumoconiosis, tuberculosis, virus infection-induced pulmonary fibrosis, post-COVID pulmonary fibrosis, liver fibrosis associated with cirrhosis, drug-induced toxicity, alcoholic liver disease, non-alcoholic fatty liver disease, non-alcoholic steatohepatitis, primary sclerosing cholangitis and non-cirrhotic hepatic fibrosis, myocardial fibrosis, right ventricular fibrosis, congenital heart disease, congestive heart failure, myocarditis, peritoneal fibrosis, encapsulating peritoneal sclerosis, kidney fibrosis associated with diabetic nephropathy, lupus nephritis, chronic kidney disease, hypertensive nephrosclerosis, chronic glomerulonephritis, cyclosporine nephrotoxicity, renal allograft rejection, tubulointerstitial fibrosis, polycystic kidney disease, glomerulosclerosis, renal vasculitis, eosinophilic granulomatosis with polyangiitis or Churg-Strauss syndrome, skin fibrosis associated with acne, blisters, hives, actinic keratosis, eczema, rosacea, latex allergy, acute mechanical skin injury, frostbite, psoriasis, contact dermatitis, vitiligo, warts, chickenpox, seborrheic eczema, seborrheic dermatitis, keratosis pilaris, melasma, impetigo, fifth disease, perniosis, Raynaud's syndrome, rashes and burns, Dupuytren's contracture, keloid, scleroderma, atopic dermatitis, pressure wounds, eczema; and fibrosis of other organ systems, mediastinal fibrosis, retroperitoneal fibrosis, myelofibrosis, nephrogenic systemic fibrosis, progressive massive fibrosis, scleroderma/progressive systemic sclerosis (PSS), and/or organ transplant rejection;

g) the dual receptor antagonist of DP2 and TP receptors is an antithrombotic, immunomodulatory and anti-inflammatory agent to prevent and/or treat carcinomas, sarcomas, leukemias and lymphomas and/or associated paraneoplastic syndromes;

h) the dual receptor antagonist of DP2 and TP receptors is as an antithrombotic, immunomodulatory and anti-inflammatory agent to prevent and/or treat hereditary diseases, osteopetrosis, muscular dystrophy, Duchenne muscle dystrophy, Becker muscular dystrophy, Limb-Girdle muscular dystrophy; hemolytic diseases, alpha thalassemia, beta thalassemia, sickle cell disease and hereditary amyloidosis and i) the dual receptor antagonist of DP2 and TP receptors is an anti-inflammatory and analgesic agent to prevent and/or treat mechanical hyperalgesia, allodynia, heat hyperalgesia, cold hyperalgesia, deep-tissue andmusculoskeletal hypoalgesia, hyperpathia, hyperesthesia, dysesthesia associated with pain crises in sickle cell disease, diabetic neuropathy, fibromyalgia, peripheral neuropathy, neuropathic pain, effects of ethanol and heavy metals; post-amputation pain/phantom limb pain, spinal cord injury, nerve trauma, stroke and opioid induced hyperalgesia.

19. The method as claimed in claim 1, wherein the dual receptor antagonist of DP2 and TP receptors is used to prevent and/or treat a metabolic disease, obesity and an obesity related disease, type II diabetes, adynamic bone disease, aspirin resistance, hypertension, hyperlipidemia and obesity induced end organ damage to heart, kidneys and liver, AA amyloidosis, hereditary amyloidosis, wild-type amyloidosis or localized amyloidosis affecting the heart, lungs, liver, skin, kidneys, brain and/or other organs; retinal inflammation and/or deafness.

20. The method as claimed in claim 1, wherein the dual receptor antagonist of DP2 and TP receptors is used to treat a neuropsychiatric disease, sickness behavior associated with infectious and autoimmune diseases, diabetes, tumors, pregnancy and/or psychological and psychiatric disease.

21. The method as claimed in claim 1, wherein said disease or condition is selected from sepsis, septic shock, toxic shock syndrome, viremia, bacterial infections, bacteremia, fungemia, endotoxemia, MODS, SIRS, post-sepsis syndrome, long-haul COVID and/or brain fog.

22. The method as claimed in claim 1, wherein said disease or condition diabetes mellitus type I or type 2 diabetes and complications of diabetes, diabetic foot, obesity due to diabetes, insulin resistance, type 2 diabetes and/or aspirin resistance.

23. The method as claimed in claim 4, directed to preventing and/or treating a respiratory disease, acute lung injury, hospital-acquired pneumonia, acute respiratory distress syndrome, cystic fibrosis, acute asthma, emphysema, chronic pulmonary emphysema, chronic obstructive pulmonary disease, chronic bronchitis and/or smoking/smoking inducing lung injury, pneumoconiosis, community-acquired pneumonia, and/or primary or secondary pulmonary hypertension.

24. The method according to claim 1 wherein the disease or condition is a fibrosis-associated disease, fibrothorax, pulmonary fibrosis, cystic fibrosis, idiopathic pulmonary fibrosis, silicosis, radiation-induced lung injury and/or pneumoconiosis.

25. The method according to claim 5 wherein dual receptor antagonist of both receptors DP2 and TP is formulated as an aerosol, inhaler, or nebulizer.

26. The method according to claim 25 wherein the dual receptor antagonist of both receptors DP2 and TP is ramatroban, a pharmaceutically acceptable salt or a derivative thereof.

* * * * *